United States Patent [19]

Kluge et al.

[11] Patent Number: 4,567,264
[45] Date of Patent: Jan. 28, 1986

[54] CARDIOSELECTIVE ARYLOXY- AND ARYLTHIO-HYDROXYPROPYLENE-PIPERAZINYL ACETANILIDES WHICH AFFECT CALCIUM ENTRY

[75] Inventors: Arthur F. Kluge, Los Altos; Robin D. Clark, Palo Alto; Arthur M. Strosberg, Menlo Park, all of Calif.; Jean-Claude G. Pascal, Cachan, France; Roger Whiting, Edinburgh, Scotland

[73] Assignee: Syntex (U.S.A.) Inc., Palo Alto, Calif.

[21] Appl. No.: 495,904

[22] Filed: May 18, 1983

[51] Int. Cl.⁴ .................. C07D 241/04; A61K 31/495
[52] U.S. Cl. .................................... 544/400; 514/255; 544/377
[58] Field of Search ................ 544/377, 400; 424/250; 514/255

[56] References Cited

U.S. PATENT DOCUMENTS

| | | | |
|---|---|---|---|
| 3,360,529 | 12/1967 | Gardner | 260/340.3 |
| 3,496,183 | 2/1970 | Toldy et al. | 260/268 |
| 3,829,441 | 8/1974 | Gardner | 260/340.3 |
| 3,869,459 | 3/1975 | Milkowski et al. | 260/268 R |
| 3,879,401 | 4/1975 | Archibald et al. | 260/293.64 |
| 3,944,549 | 3/1976 | Lafon | 260/256.4 N |
| 4,059,621 | 11/1977 | Vincent et al. | 260/558 R |
| 4,096,259 | 6/1978 | Buzas et al. | 544/377 |
| 4,178,442 | 12/1979 | Bourgery et al. | 544/377 |
| 4,302,469 | 11/1981 | Kluge et al. | 424/273 R |
| 4,315,939 | 2/1982 | Frickel et al. | 424/267 |
| 4,335,126 | 6/1982 | Kleemann | 424/250 |
| 4,353,901 | 10/1982 | Clark | 424/248.57 |
| 4,353,904 | 10/1982 | Thieme et al. | 424/250 |
| 4,374,837 | 2/1983 | Favier et al. | 424/253 |

FOREIGN PATENT DOCUMENTS

| | | |
|---|---|---|
| 806380 | of 0000 | Belgium . |
| 0025111 | 3/1981 | European Pat. Off. . |
| EP61149 | 9/1982 | European Pat. Off. . |
| 0068544 | 1/1983 | European Pat. Off. . |
| 2942832 | 4/1980 | Fed. Rep. of Germany . |
| 2267104 | 11/1975 | France . |
| 2456738 | 12/1980 | France . |
| 1332008 | 10/1973 | United Kingdom . |
| 1387735 | 3/1975 | United Kingdom . |
| 1434580 | 5/1976 | United Kingdom . |
| 2067562 | 8/1979 | United Kingdom . |
| 2057433 | 4/1981 | United Kingdom . |

OTHER PUBLICATIONS

Stankeviciene et al., Chem. Abstracts vol. 90, p. 608, 5407c, Synthesis of N-(3-Aryloxy-2-Hydroxypropyl-)-1-Piperazines.
Turin et al., Chem. Abstracts vol. 77, p. 437, 101669v.
Tshiguro et al., Chem. Abstracts, vol. 85, p. 641, 94405r.
L. Stankeviciene et al., "Synthesis of N-Arloxy-2-Hydroxypropyl-1-Piperazines", *Mater. Mezvug. Nauchv. Konf. Kaunes. Med. Inst.*, 25th (1976), publ. 1977, pp. 322-3, [Chem. Abst. 90, 54907c, (1979)].
J. M. Caroon et al., "Synthesis and Antihypertensive Activity of a Series of 8-Substituted 1-Oxa-3,8-Diazaspiro [4,5]Decan-2-Ones," *J. Med. Chem.*, 24, 1320-1328, (1981).

*Primary Examiner*—Donald G. Daus
*Assistant Examiner*—Cecilia Shen
*Attorney, Agent, or Firm*—Charles L. Hartman; Tom M. Moran; Alan M. Krubiner

[57] ABSTRACT

Novel compounds of the general formula

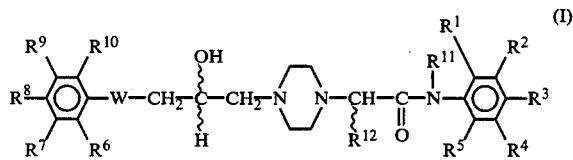

and the pharmaceutically acceptable esters and acid addition salts thereof, wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, N-optionally substituted alkylamido, except that when $R^1$ is methyl, $R^4$ is not methyl; or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di-lower alkyl amino; or $R^6$ and $R^7$ together form —CH=CH—CH=CH—;

$R^7$ and $R^8$ together form —OCH$_2$O—;

$R^{11}$ and $R^{12}$ are each independently hydrogen or lower alkyl; and

W is oxygen or sulfur.

These cardioselective compounds have calcium entry blockade properties and therefore are useful in therapy in the treatment of cardiovascular diseases, including arrhythmias, variant and exercise induced angina and myocardial infarction.

3 Claims, No Drawings

CARDIOSELECTIVE ARYLOXY- AND ARYLTHIO-HYDROXYPROPYLENE-PIPERAZINYL ACETANILIDES WHICH AFFECT CALCIUM ENTRY

BACKGROUND OF THE INVENTION

The present invention is concerned with compounds, compositions, and methods useful for treating diseases in human beings which are affected by calcium entry blockade. In particular, compounds wherein piperazine is bound through one nitrogen to an aryloxy or arylthio moiety by a hydroxypropyl or alkanoyloxypropylene linkage, and through the other nitrogen to an acetanilide residue are useful in this regard.

Large numbers of compounds are known which affect various physiological systems related to adrenergic control. Compounds which are related to the compounds of the present invention are disclosed in Belgian Pat. No. 806,380 (U.S. Pat. No. 3,944,549), and include 1-(1,4-benzodioxan-2-ylmethyl)-4-(2,6-dimethylphenylacetanilido)piperazine; in L. Stankeviciene, et al. in *Mater. Mezhvug. Nauchv. Konf. Kaunos. Med. Inst.*, 25th (1976), published in 1977, pages 322-3 [*Chem. Abstr.*, 90, 54907c (1979)]; and French Pat. No. 2,267,104. Additional references of interest in this art include U.S. Pat. Nos. 3,360,529; 3,496,183; 3,829,441; 3,879,401; 3,944,549; 4,059,621; 4,302,469; 4,315,939; 4,335,126; and 4,353,901, all of which are incorporated herein by reference. Calcium entry blocking compounds have been used to mediate the symptoms of cardiovascular diseases, such as, myocardial infarction, congestive heart failure, angina and arrhythmia. The present invention concerns a group of cardioselective compounds which are useful in the treatment of these cardiovascular diseases.

SUMMARY OF THE INVENTION

In one aspect this invention concerns piperazine derivatives of the general formula:

$$R^9\text{-}R^{10}\text{-aryl-W-CH}_2\text{-C(OH)(H)-CH}_2\text{-N(piperazine)N-CH(R^{11})-C(R^{12})(O)-N-aryl-R^1R^2R^3R^4R^5}\quad (I)$$

and the pharmaceutically acceptable esters and acid addition salts thereof, wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, N-optionally substituted alkylamido, except that when $R^1$ is methyl, $R^4$ is not methyl; or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di-lower alkyl amino;

$R^6$ and $R^7$ together form —CH=CH—CH=CH—; or $R^7$ and $R^8$ together form —OCH$_2$O—; $R^{11}$ and $R^{12}$ are each independently hydrogen or lower alkyl; and W is oxygen or sulfur.

These cardioselective compounds are useful in therapy in the treatment of cardiovascular diseases, including arrhythmias, variant and exercise induced angina and myocardial infarction.

Another aspect of this invention is a process for the preparation of compounds of formula I, as described in more detail hereinafter.

DETAILED DESCRIPTION OF THE INVENTION

Definitions

As used herein:

"Aminocarbonylmethyl" refers to a group having the following structure $$-CH_2-\underset{\underset{\displaystyle O}{\|}}{C}-NH_2.$$

"Aryl" refers to an optionally substituted phenyl or naphthyl group where $R^6$ and $R^7$ together form —CH=CH—CH=CH—.

"Cyano" refers to a group having the following structure —C≡N.

"Di-lower alkyl amino" refers to a group having the following structure $R^{13}(R^{14})N$— wherein $R^{13}$ and $R^{14}$ are each independently lower alkyl as defined herein.

"Halo" or "halogen" refers to fluoro, chloro, bromo or iodo usually regarding halo substitution for a hydrogen atom in an organic compound.

"Isomerism" refers to compounds having the same atomic mass and atomic number but differing in one or more physical or chemical properties. Various types of isomerism include the following:

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d-, l-, or a d,l-pair or D-, L- or a D,L-pair; or R-, S-, or an R,S-pair, depending upon the nomenclature system employed.

"Diastereoisomer" refers to stereoisomers some or all of which are dissymmetric but which are not mirror images of each other. Diastereoisomers corresponding to a given structural formula must have at least two asymmetric atoms. A compound having two asymmetric atoms will usually exist in four diastereoisomeric forms, i.e. (−)-erythro, (+)-erythro, (−)-threo and (+)-threo.

Certain compounds of formula I wherein $R^{12}$ is hydrogen will have one asymetric carbon atom, i.e., the carbon atom 2 of the propyl moiety. These compounds will exist in two stereochemical forms; i.e., (+) and (−) or R and S— and mixtures thereof. Compounds of formula I where $R^{12}$ is a group other than hydrogen will have two asymmetric carbon atoms, i.e. the carbon atom at the 2 position of the propyl moiety, and the carbon atom to which $R^{12}$ is attached. These compounds may exist in four stereochemical forms (+)-erythro-, (−)-erythro-, (+)-threo-, (−)-threo and mixtures thereof. The Cahn-Prelog convention will describe these four isomers as R-R, R-S, S-R, and S-S, which denotes the stereochemistry at each of the asymmetric carbon atoms. The R and S designation will be used in this application. This patent application is to be interpreted to include the individual stereoisomers as well as mixtures thereof.

"Structure of formula I" refers to the generic structure of the compounds of the invention. The chemical bonds indicated as ( ≶ ) in formula I indicate the nonspecific stereochemistry of the asymmetric carbon atoms, e.g. at position 2 of the propyl chain, i.e., the carbon to which is attached the hydroxyl (—OH) group, and the carbon to which $R^{12}$ is attached between the piperazine ring and the carbonyl group.

"Lower acyl" refers to a group having the following structure

wherein $R^{15}$ is lower alkyl as is defined herein, and includes such groups as acetyl, propanoyl, n-butanoyl and the like.

"Lower alkyl" refers to a unbranched saturated hydrocarbon chain of 1–4 carbons, such as, for example, methyl, ethyl, n-propyl, and n-butyl.

"Lower alkoxy" refers to a group —OR wherein R is lower alkyl as herein defined.

"Lower alkylthio" refers to a group —SR wherein R is lower alkyl as herein defined.

"Lower alkyl sulfinyl" refers to

wherein R is lower alkyl as herein defined.

"Lower alkyl sulfonyl" refers to

wherein R is lower alkyl as herein defined.

"N-Optionally substituted alkylamido" refers to a group having the following structure

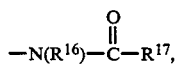

wherein $R^{16}$ is independently hydrogen or lower alkyl and $R^{17}$ is lower alkyl as defined herein.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Pharmaceutically acceptable ester" of the compound of formula I which may conveniently be used in therapy includes those containing the alkanoyloxy group, —O—C(=O)—Z, wherein Z is an alkyl group containing 1 to 12 carbon atoms, which is attached to carbon atom 2 of the propylene linkage instead of the hydroxyl group, i.e., the hydroxy group has been esterified. The group, Z, may be for example, methyl, ethyl, butyl, hexyl, octyl, dodecyl and the like. This invention contemplates those compounds of formula I which are esters as described herein and at the same time are the pharmaceutically acceptable acid addition salts thereof.

"Piperazino" structure describes the following saturated six-membered dinitrogen substituted heterocyclic moiety:

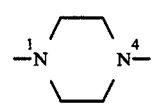

The compounds of the present invention are generally named according to the IUPAC nomenclature system. The locants for the substituents on the ring system of the above compounds of the instant invention are as depicted in the Summary of the Invention above. For example, when $R^1$ and $R^5$ are methyl, $R^6$ is methoxy, $R^2$ to $R^4$ and $R^7$ to $R^{12}$ are hydrogen, and W is oxygen, the compound of formula I is named 1-[3-(2-methoxyphenoxy-2-hydroxypropyl]-4-[(2,6-dimethylphenyl)aminocarbonylmethyl]piperazine, and is shown below:

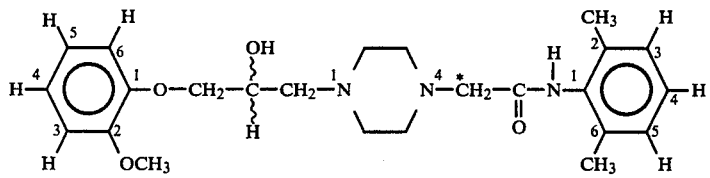

where * denotes a center or possible center of asymmetry. This compound may also be named as 1-[3-(2-methoxyphenoxy)-2-hydroxypropyl]-4-(2,6-dimethylphenylcarbamoylmethyl)piperazine; or 1-[3-(2-methoxyphenoxy)-2-hydroxypropyl]-4-(2,6-dimethylacetanilido)piperazine. For purposes of this patent application, the IUPAC designation first described above will be used.

The optically active compounds herein can be designated by a number of conventions; i.e., the R- and S-sequencing rules of Cahn and Prelog; erythro and threo isomers; D- and L-isomers; d- and l-isomers; and (+) and (−)-isomers, which indicates the direction a plane of polarized light is rotated by the chemical structure, either pure or in solution. These conventions are well-known in the art and are described in detail by E. L. Eliel in *Stereochemistry of Carbon Compounds*, published by McGraw Hill Book Company, Inc. of New York in 1962 and references cited therein.

In the Reaction Sequences as discussed herein:

"$Ar^1$" represents the aryl moiety which may optionally be substituted by $R^6$ to $R^{10}$ as defined hereinabove. The linkage to other parts of the molecule is through the carbon atom at the 1 position, i.e., to the oxygen or sulfur atom, and the other numbered positions of the aryl group are indicated, as shown:

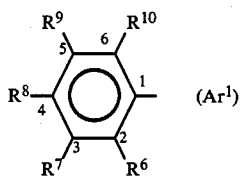

"$Ar^2$" represents an optionally substituted phenyl group wherein $R^1$ to $R^5$ are as defined hereinabove, and the other numbered positions are shown.

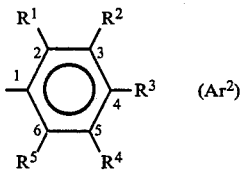

DETAILED DESCRIPTION AND PRESENTLY PREFERRED EMBODIMENTS

Preferred embodiments of the present invention include those compounds of formula I wherein two substitutents selected from $R^1$ to $R^5$ are hydrogen and two substituents selected from $R^6$ to $R^{10}$ are hydrogen. A preferred subgroup are those compounds of formula I wherein W is oxygen; i.e., O.

A preferred subgroup are those compounds of formula I wherein the substituents $R^2$, $R^3$ and $R^4$ are hydrogen.

A preferred subgroup are those compounds wherein two substituents $R^1$ and $R^5$ are each lower alkyl, particularly methyl.

A presently preferred compound of the present invention includes those compounds of formula I wherein substituents $R^1$ and $R^5$ are each methyl, $R^2$, $R^3$, $R^4$ and $R^6$ to $R^{12}$ are each hydrogen and W is O; i.e., 1-[3-phenoxy-2-hydroxypropyl]-4-[(2,6-dimethylphenyl)aminocarbonylmethyl]piperazine.

A presently preferred compound of the present invention includes those compounds of formula I wherein $R^1$ and $R^5$ are each methyl, $R^6$ is methoxy, $R^2$, $R^3$, $R^4$ and $R^7$ to $R^{12}$ are each hydrogen and W is O; i.e., 1-[3-(2-methoxyphenoxy)-2-hydroxypropyl]-4-[(2,6-dimethylphenyl)aminocarbonylmethyl]piperazine.

A presently preferred compound of the present invention includes those compounds of formula I wherein $R^1$ and $R^5$, are each methyl, $R^6$ is cyano, $R^2$, $R^3$, $R^4$ and $R^7$ to $R^{12}$ are each hydrogen and W is O; i.e., 1-[3-(2-cyanophenoxy)-2-hydroxypropyl]-4-[(2,6-dimethylphenyl)aminocarbonylmethyl]piperazine.

Preferred embodiments include those compounds of formula I wherein the substituents $R^1$, $R^4$ and $R^5$ are hydrogen.

Preferred embodiments include those compounds of formula I wherein two non-hydrogen substituents $R^2$ and $R^3$ are each halo, particularly chloro.

Preferred embodiments include those compounds of formula I wherein a maximum of one non-hydrogen substitutent is selected from $R^1$ to $R^5$. A presently preferred subgroup includes those compounds of formula I wherein one non-hydrogen substituent is $R^1$. A preferred subgroup includes those compounds of formula I wherein one substituent is lower alkoxy, particularly methoxy.

Embodiments of the present invention include those compounds of formula I wherein two non-hydrogen substituents are $R^7$ to $R^9$. A preferred subgroup are those compounds wherein $R^6$ and $R^{10}$ are lower alkoxy, particularly methoxy.

Preferred embodiments include those compounds of formula I wherein a maximum of one non-hydrogen substituent is selected from $R^6$ to $R^{10}$.

A preferred subgroup includes those compounds of formula I wherein one non-hydrogen substituent $R^6$ is lower alkoxy, particularly methoxy.

A preferred subgroup includes those compounds of formula I wherein the substituent $R^6$ is cyano or halo, particularly chloro.

A preferred subgroup of the present invention includes those compounds of formula I wherein the non-hydrogen substituent $R^8$ is lower alkoxy, particularly methoxy, or chloro.

Embodiments of the present invention include those compounds of formula I wherein $R^{11}$ is hydrogen.

Embodiments of the present invention include those compounds of formula I wherein $R^{12}$ is hydrogen.

Embodiments of the present invention include those compounds of formula I wherein $R^{11}$ and $R^{12}$ are both hydrogen.

Embodiments of the present invention include those compounds of formula I wherein W is sulfur, i.e., S.

Presently preferred subgroups include those compounds wherein $R^{12}$ is lower alkyl, particularly methyl; and wherein $R^{11}$ and $R^{12}$ are each lower alkyl, particularly methyl. Particularly preferred sulfur-containing compounds include:

1-[3-(phenythio)-2-hydroxypropyl]-4-[(phenyl)aminocarbonyl-1-ethyl]piperazine; and 1-[3-(phenylthio)-2-hydroxypropyl]-4-[N-methyl-N-(phenyl)-aminocarbonyl-1-ethyl]piperazine.

Presently preferred compounds of the present invention are those wherein $R^6$, $R^7$, $R^8$, $R^9$ and $R^{10}$ are each hydrogen. Particularly preferred compounds of this sub-group are those wherein $R^1$ to $R^{10}$ are all hydrogen.

Another presently preferred group of compounds are those wherein $R^{11}$ is hydrogen. Of this subgroup, those presently preferred are those compounds wherein all of $R^1$ to $R^{10}$ are hydrogen. Preferred among these are compounds wherein $R^{11}$ is also hydrogen.

Especially preferred from those compounds wherein $R^{11}$ is hydrogen are the compounds selected from the group comprising:

1-[3-(2-methoxyphenoxy)-2-hydroxypropyl]-4-[(2,6-dimethylphenyl)aminocarbonylmethyl]piperazine;

1-[3-(2-methoxyphenoxy)-2-hydroxypropyl]-4-(phenylaminocarbonylmethyl)piperazine;

1-[3-(2-methoxyphenoxy)-2-hydroxypropyl]-4-[(4-chlorophenyl)aminocarbonylmethyl]piperazine;

1-[3-(2-methoxyphenoxy)-2-hydroxypropyl]-4-[(4-methylphenyl)aminocarbonylmethyl]piperazine;

1-[3-(2-methoxyphenoxy)-2-hydroxypropyl]-4-[(4-methoxyphenyl)aminocarbonylmethyl]piperazine;

1-[3-(2-methoxyphenoxy)-2-hydroxypropyl]-4-[(2,6-dichlorophenyl)aminocarbonylmethyl]piperazine;

1-[3-(2-methoxyphenoxy)-2-hydroxypropyl]-4-[(4-trifluoromethylphenyl)aminocarbonylmethyl]piperazine;

1-[3-(2-ethylsulfinylphenoxy)-2-hydroxypropyl]-4-[(phenyl)aminocarbonylmethyl]piperazine;

1-[3-(2-methoxyphenoxy)-2-hydroxypropyl]-4-[(3,4-methylenedioxyphenyl)aminocarbonylmethyl]piperazine; or 1-[3-(1-naphthyl)-2-hydroxypropyl]-4-[(2,6-dimethylphenyl)aminocarbonylmethyl]piperazine.

An additional set of presently preferred compounds are those wherein $R^{11}$ and $R^{12}$ are methyl; presently preferred among these is:

1-[3-(2-methoxyphenoxy)-2-hydroxypropyl]-4-[(2,6-dimethylphenyl)-N-(methyl)aminocarbonyl-1-ethyl]piperazine.

A pharmaceutical composition useful for treating one or more cardiovascular diseases, such as arrhythmia, myocardial infarction and variant and exercise-induced angina, in a mammal, particularly a human being, which comprises a therapeutically effective amount of a compound of formula I or a pharmaceutically acceptable acid addition salt thereof in admixture with a pharmaceutically acceptable excipient.

A method for treating a cardiovascular disease, such as arrhythmia, myocardial infarction and variant and exercise-induced angina, in a mammal, particularly a human being, which method comprises administering to a subject in need of such treatment a therapeutically effective amount of the compound of formula I or a pharmaceutically acceptable acid addition salt thereof.

These embodiments also include the optical isomers (+) and (−) and R- and S- isomers and mixtures thereof. This invention includes the individual isomers and all possible mixtures thereof.

All of the aforementioned embodiments include the pharmaceutically acceptable esters and acid addition salts thereof, particularly the mono- and dihydrochlorides, and mixtures thereof.

Process for Preparation

Reaction Sequence(s) 1 and 2 shown below, are complementary processes for linking the two "halves" of the compounds of formula I through the piperazine ring.

In the Reaction Sequence(s) below, X represents a leaving group such as, for example, halo or sulfonyl ester group, preferably a halo group. The starting materials for these reaction sequence(s) are obtained as described below.

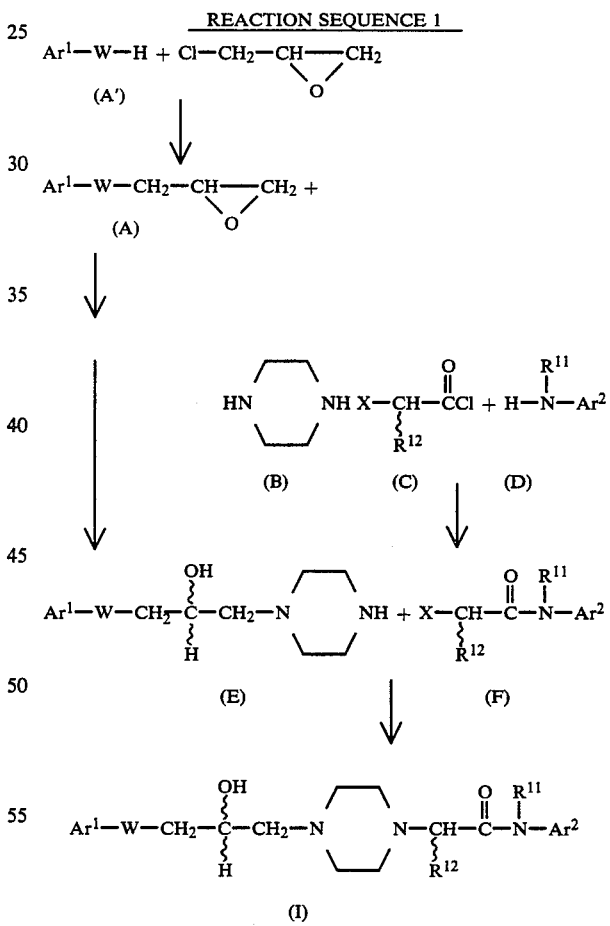

Reaction Sequence 1

The compound of formula A wherein $Ar^1$ is as described above is obtained by reacting the appropriate phenol and 2,3-isopropylidinyl-1-tosylpropane, hydrolysis with aqueous acid, then by reaction with methanesulfonyl chloride or toluenesulfonyl chloride and pyridine followed by reaction with sodium hydroxide, as is well known to those in the art ([see, for example, Carroon et al., *J. Med. Chem.* 24, 1320 (1981)].

The intermediate aryloxy and arylthio epoxide compounds (formula A) are also prepared by reacting the unsubstituted or substituted phenol or thiophenol with epichlorohydrin in the presence of a strong base, such as TRITON B, trialkyl amines, alkali metal hydroxides, alkoxides or hydrides, for example, sodium or potassium hydroxide, methoxide or hydride. The reaction is run in an inert solvent such as methanol, ethanol, dimethylformamide, dimethylsulfoxide and the like at ambient temperature for about 20 hours, [See, for example, G. Shtacher, et al, *J. Med. Chem.*, Vol. 16, No. 5, p. 516ff (1973)].

The phenols and thiophenols are readily available or if not readily available may be prepared by methods well known in the art. For example, many of the substituted phenols are commercially available. These include the methyl-, dimethyl-, trimethyl-, ethyl-, diethyl-, propyl-, butyl-, methoxy-, dimethoxy-, trimethoxy-, ethoxy-, diethoxy-, propoxy-, butoxy-, cyano, chloro-, dichloro-, trichloro-, tetrachloro-, pentachloro-, bromo-, dibromo-, tribromo-, fluoro-, difluoro-, trifluoro-, bromochloro-, bromofluoro-, chlorofluoro-, methylthio-, methylenedioxy- phenols and mixtures of the aforementioned compounds, according to *Chemical Sources*, published by Directories Publishing Company, Inc., Flemington, New Jersey in 1979.

The methylsulfinyl and methylsulfonyl substituted phenols are prepared according to conventional procedures known in the art starting from the corresponding methylthiophenol, which is available from commercial sources or can be readily prepared. For instance, the o-methylsulfinylphenol is prepared by treating o-methylthiophenol with acetic anhydride to form the corresponding ester which is then treated with sodium periodate in methanol. Upon hydrolysis to remove the acetyl group using acidic or basic conditions, there is obtained o-methylsulfinylphenol. The o-methylsulfonyl phenol is obtained by treating the ester prepared above with hydrogen peroxide or 2-chloroperbenzoic acid in aqueous methanol. After hydrolysis to remove the acetyl group, there is obtained o-methylsulfonylphenol in good yield. The corresponding m- and p- substituted methylsulfinylphenols and methylsulfonylphenols are prepared by replacement of o-methylthiophenol by m-methyl- and p-methylthiophenol respectively.

These compounds of formula A can then be converted into the materials of formula E in Reaction Sequence 1 by reacting the resulting phenoxy substituted epoxide derivatives with piperazine (formula B), by heating in a solvent that will dissolve both reactants, using methods known to those in the art. (See Caroon et al., supra)

The compounds of formula F are prepared from the corresponding aniline, substituted aniline, or N-substituted aniline derivatives, of formula D which are commercially available, by reaction with α-haloacyl halides, such as monochloroacetyl chloride, or α-chloropropionyl chloride (compounds of formula C).

Many of the substituted anilines are commercially available. These include the methyl-, dimethyl-, trimethyl-, ethyl-, diethyl-, propyl-, butyl-, methoxy-, dimethoxy-, trimethoxy-, ethoxy-, diethoxy-, propoxy-, butoxy-, chloro-, dichloro-, trichloro-, tetrachloro-, pentachloro-, bromo-, dibromo-, tribromo-, fluoro-, difluoro-, trifluoro-, bromochloro-, bromofluoro-, chlorofluoro-, methylthio-, methylenedioxy- anilines and mixtures of the aforementioned compounds. Many N-alkylated aniline derivatives such as the N-methyl-, N-ethyl-, N-propyl- and N-butyl- anilines and substituted anilines are also commercially available according to *Chemical Sources*, published by Directories Publishing Company, Inc., Flemington, New Jersey in 1979.

The methylsulfinyl and methylsulfonyl substituted anilines are prepared according to conventional procedures known in the art starting from the corresponding methylthioaniline, which is available from commercial sources. For instance, the o-methylsulfinylaniline is prepared by treating o-methylthioaniline with acetic anhydride to form the corresponding acetanilide which is then treated with sodium periodate in methanol. Upon hydrolysis to remove the acetyl group using acidic or basic conditions, there is obtained o-methylsulfinylaniline. The o-methylsulfonyl aniline is obtained by treating the acetanilide prepared above with hydrogen peroxide or 2-chloroperbenzoic acid in aqueous methanol. After hydrolysis to remove the acetyl group, there is obtained o-methylsulfonylaniline in good yield. The corresponding m- and p- substituted methylsulfinylanilines and methylsulfonylanilines are prepared by replacement of o-methylthioaniline by m-methyl and p-methylthioaniline respectively.

The corresponding ethyl-, propyl- and butylthioanilines are prepared by treatment of the commercially available aminothiophenol with sodium hydroxide followed by the appropriate alkyl iodide. The corresponding ethyl-, propyl- and butyl-sulfinyl and sulfonylanilines are prepared by replacement of o-methylthioaniline with the appropriate alkylthioaniline in the procedures described above.

Many N-alkyl substituted anilines may be prepared by procedures known in the art, such as treatment of the unsubstituted or aryl-substituted anilines described herein using an alkyl halide such as methyl chloride, ethyl chloride, propyl chloride, butyl chloride or the like in a suitable solvent such as diethylether or methylene dichloride.

Many α-halo acid halides are commercially available, including for example, chloroacetyl chloride and 2-chloropropionyl chloride. 2-Chlorobutyric acid is commercially available and may be converted to the acid chloride by methods known in the art, such as reaction with thionyl chloride or phosphorus pentachloride. The α- or 2-chloroacid chlorides which are not readily available may be prepared by conventional methods such as the Hell-Volhard-Zelinsky Reaction in which the appropriate alkyl carboxylic acid is reacted with chlorine in the presence of phosphorus. See for example, *Organic Chemistry*, by R. T. Morrison and R. N. Boyd, 2nd Edition, Ch. 18, p 604, and *Chem. Revs.*, Vol 7, p 180 (1930).

To carry out this reaction to produce compounds of formula F, the aniline derivative, a basic amine, such as triethylamine or pyridine, preferably triethylamine, and the chloroacyl chloride are dissolved in an inert aprotic organic solvent, such as, for example, benzene, chloroform, carbon tetrachloride, methylene or methylene chloride, preferably methylene chloride. The aniline and tertiary amine are in approximately equimolar amounts, and the acyl chloride is added in slight molar excess, about 1.2 or 2 molar excess, preferably 1.3 to 1.5 molar excess compared to the aniline. The mixture is cooled to about $-10°$ C. to $+30°$ C., preferably in an ice bath, before the addition of the acyl halide. The mixture is maintained at this low temperature for approximately 0.5 to 8 hours, preferably about 4 hours with stirring. The resulting condensed product, of formula F, is then isolated by conventional means.

Compounds of formula I wherein $Ar^1$, $Ar^2$, $R^1$ to $R^{12}$ and W are as defined above are prepared by reacting compounds of formula E with compounds of the formula F in the presence of a solvent such as toluene/methanol mixture, ethanol and dimethylformamide and the like. The reaction mixture is heated to a temperature of about 60° C. to about 150° C., preferably to about 70° C. to about 90° C. for about 6 hours to about 24 hours.

Isolation and purification of the compounds and intermediates described can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to dryness, and the salts can be further purified by conventional methods.

The compounds of formula I produced by any of the Reaction Sequences described herein may exist as R- or S- isomers (or erythro and threo isomers). Accordingly, the compounds of the present invention may be prepared in either the R- or S- forms or as mixtures thereof. Unless specified, the compounds of the instant invention are a mixture of R- and S- forms. However, the scope of the subject invention is not considered to be limited to the R-/S- mixture but encompasses the individual isomers of the subject compounds as well.

If desired, a mixture of the intermediates used to prepare compounds of formula I or the final product may be separated by, e.g., recrystallization and chromatography. It is preferred to prepare the individual isomers from the isomeric intermediates of the compound of formula I.

Reaction Sequence 2

Alternatively, the compounds of formula I may be prepared according to Reaction Sequence 2 wherein $Ar^1$, $Ar^2$, $R^1$ to $R^{12}$ and W are as described above.

REACTION SEQUENCE 2

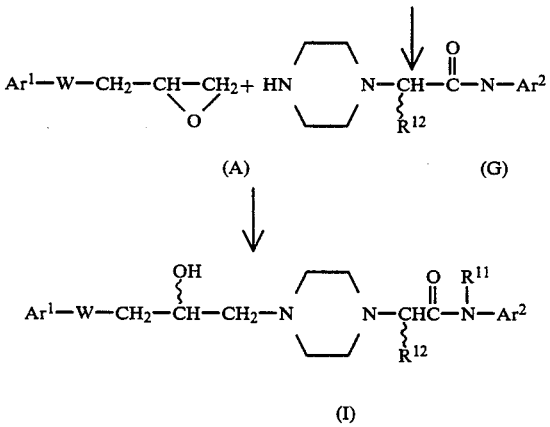

The compounds of formula F are produced by the reaction of a compound of formula C and a compound of formula D as was described above in Reaction Sequence 1.

The compounds of formula G are prepared from the corresponding compounds of formula F by reaction with piperazine (formula B), by means well known to those in the art, similar to those utilized in converting the compounds of formula E and F into compounds of formula I. In this procedure, in both cases, the halide is mixed with an excess of piperazine or a substituted piperazine, specifically about a 3 to 5 molar excess, preferably about a 4 molar excess in a polar organic solvent, such as ethanol or propanol, preferably ethanol or ethanol/water (50/50), and the mixture is heated to 50° to 100°, preferably the reflux temperature of the solvent for 1 to 4 hours, preferably about 2 hours. The product of formula G may be isolated by conventional means.

The compounds of formula I are then prepared and isolated in a manner similar to that described above for the reaction of compounds of formulas A and B in Reaction Sequence 1 by combining the compounds of formulas A and G.

The coupling step, usually the final step, of the processes of Reaction Sequences 1 and 2, is carried out in substantially similar fashion to each other. The compounds of formulas E and F or alternatively the compounds of formula A and G are combined in essentially equimolar amounts in an aprotic organic polar solvent, such as, for example, dimethylformamide, tetrahydrofuran, and the like, preferably dimethylformamide. The reaction mixture is heated to about 50° to about 100°, preferably about 60° to about 70° and then the temperature raised to about 70° to 110°, preferably 85 to 95° and allowed to react for about 1 to about 24 hours, preferably overnight. The condensed product of formula I is then isolated by conventional means.

The compounds of formula I described herein may exist as mixtures of optical isomers because of the possible two asymmetric carbon atoms. Accordingly, the compounds of the present invention may be prepared in either optically active form or as racemic mixtures. Unless otherwise specified, the compounds described herein are all in the racemic form. However, the scope of the subject invention herein is not considered to be limited to a mixture of the racemic forms but to encompass all of the individual optical isomers as well.

If desired, racemic intermediates of compounds of formula A, A', C, E, F or G (supra) or final product, i.e., formula I prepared herein may be resolved into their optical antipodes by conventional resolution means known in the art, for example, by the separation (e.g., fractional crystallization) of the diastereomeric salts formed by reaction of, e.g., racemic compounds of formula I or the intermediate compounds of formula A, A', C, E, F or G (supra) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acids, and the like and, where necessary, bases such as cinchonidine, brucine or the like. The separated pure diastereomeric salts may then be cleaved by standard means to afford the respective optical isomers of the compounds of formula I or the intermediates of formula A, A', C, E, F or G (supra).

The compounds of formula I may be isolated as free bases, but it is usually more convenient to isolate the compounds of the instant invention as acid addition salts. These salts are prepared in the usual manner, i.e., by reaction of the free base with a suitable organic or inorganic acid, for example, one of the pharmaceutically acceptable acids described above. The base of formula I, dissolved in an unreactive solvent such as an alcohol, e.g., methanol and ethanol, or an ether, e.g., diethyl ether and the like, is acidified with an acid dissolved in a like solvent. The acid solution is added until precipitation of the salt is complete. The reaction is carried out at a temperature of 20° to 50° C., preferably at room temperature. If desired, the salt can be readily converted to the free base by treatment with a base such as potassium or sodium carbonate or ammonium, potassium, or sodium hydroxide.

The compounds of formula I in free base form may be converted to the acid addition salts by treating with the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

The acid addition salts of the compounds of formula I may be decomposed to the corresponding free base by treating with a suitable base, such as potassium carbonate or sodium hydroxide, typically in the presence of aqueous solvent, and at a temperature of between about 0° C. and 100° C. The free base form is isolated by conventional means, such as extraction with an organic solvent.

The pharmaceutically acceptable esters of the compound of formula I and the pharmaceutically acceptable acid addition salts of the esters thereof are prepared by treatment with an excess, about 1.1 to about 2 equivalents of the corresponding acid anhydride or acyl halide in the presence of a catalyst such as pyridine under conditions of about −10° to about +10° C. for about 0.5 to about 12 hours, conditions which are known in the art and described in the Example below. (See for example, the appropriate sections of Morrison and Boyd, supra and Fieser and Fieser, *Reagents for Organic Synthesis,* John Wiley and Sons, Inc., New York, published in 1967.) Suitable esters which are prepared include acetates, propionates, butanoates, hexanoates, octanoates, dodecanoates and the like. The pharmaceutically acceptable acid addition salts of the esters of the compound of formula I are then prepared as described in Examples 6, 8 or 9 below.

Salts of the compounds of formula I may be interchanged by taking advantage of differential solubilities and volatilities, or by treating with the appropriately loaded ion exchange resin. This conversion is carried out at a temperature between about 0° C. and the boiling point of the solvent being used as the medium for the procedure.

In summary then, the compounds of formula I are prepared by:

reacting an unsubstituted or substituted aryloxy- or arylthio-2-hydroxypropylpiperazine (formula E) [which according to one alternative can be formed by the coupling of a 1-aryloxy- or 1-arylthio-2,3-epoxypropane (formula A) with piperazine (formula B) to form the N-substituted piperazine (formula E)]; and the substituted halo alkylanilide (formula F) [which according to one alternative can be formed by the coupling of 2-haloalkylcarboxyl halide (formula C) with the unsubstituted or substituted aniline (formula D)].

Alternatively, the compounds of formula I are prepared by:

reacting an unsubstituted or substituted 1-(aryloxy) or 1-(arylthio)-2,3-epoxypropane (formula A); and the N-substituted piperazine (formula G) [which according to one alternative can be formed by the coupling of 2-haloalkylcarboxylhalide (formula C) with the unsubstituted or substituted aniline (formula D) to produce compound of formula F which is coupled with piperazine (formula B)].

Alternatively, the compound of formula I is prepared by converting a salt of formula I to a free base by using a stoichiometric excess of a base.

Alternatively, the free base of the compound of formula I is converted to a pharmaceutically acceptable acid addition salt by use of a stoichiometric excess of an acceptable acid.

Alternatively, the salt of the compound of formula I is converted to a different salt of the compound of formula I by use of a stoichiometric excess of an acceptable different acid.

Utility and Administration

The compounds of the invention have been shown to effect calcium entry and $\beta$- blockade in experimental animal preparations, using in vitro preparations and animal tissue cultures. See for example, Kent et al., *Federation Proceedings,* Vol. 40, p. 724 (1981), Killam, et al., *Federation Proceedings,* Vol. 42, p. 1244 (1983) and Cotten et al., *Journal Pharm. Exp. Therap.,* Vol. 121, pp. 183–190 (1957). The compounds have been shown to be effective in animal models for cardiovascular diseases such as arrhythmia, angina, and myocardial infarction. These compounds are, therefore, useful in a treating cardiovascular disease, particularly myocardial infarction, variant and exercise-induced angina and arrhythmias, in a mammal, particularly a human being.

Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–10 mg/kg/day, preferably 0.5–5 mg/kg/day. For an average 70 kg human, this would amount to 7-700 mg per day, or preferably 35-350 mg/day.

Since all of the effects of the compounds herein (antiinfarction, variant and exercise induced angina inhibition and antiarrhythmia) are achieved through a similar mechanism (effecting calcium entry blockade) dosages (and forms of administration) are within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 15th Edition, 1975. The composition or formulation to be administered will, in any event, contain a quantity of the active compound(s), a therapeutically effective amount, i.e. in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 1-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference.

The following preparations and examples serve to illustrate the invention. They should not be construed as narrowing it, or limiting its scope.

PREPARATION A (Preparation of Compounds of formula A)

(a) To 2-methoxyphenol(76 g) dissolved in about 60 ml of water and 200 ml of dioxane containing 29 g of sodium hydroxide is slowly added a large excess of epichlorohydrin (80 g). The solution is stirred at reflux temperature for 3 hrs. The mixture is diluted with ether, washed with two portions of water and dried using anhydrous magnesium sulfate. Evaporation of the dried extract, followed by distillation of the residue produced the product, 1-(2-methoxyphenoxy)-2,3-epoxypropane.

(b) Similarly, proceeding as in Subpart (a) above, but substituting a stoichiometrically equivalent of:
2-methylphenol;
3-methylphenol;
4-methylphenol;
4-n-butylphenol;
2-methoxyphenol;
4-methoxyphenol;
2-isopropoxyphenol;
2-n-butoxyphenol;
2-chlorophenol;
4-chlorophenol;
4-bromophenol;
2,4-dimethylphenol;
2,4-dichlorophenol;
4-methyl-5-chlorophenol;
3,4,5-trichlorophenol;
3,4,5-trimethoxyphenol;
3-methyl-4,5-dichlorophenol;
3-methyl-4-chloro-5-methoxyphenol;
2,3,4,5-tetrabromophenol;
3,6-dimethyl-4,5-dichlorophenol;
4-trifluoromethylphenol;
4-methylthiophenol;
4-n-butylthiophenol;
4-methylsulfinylphenol;
4-n-butylsulfinylphenol;
4-methylsulfonylphenol;
4-n-butylsulfonylphenol;
2-cyanophenol;
2-acetylphenol;
4-n-butanoylphenol;
4-(N,N-dimethylamino)phenol;
4-(N,N-di-n-butylamino)phenol;
1-naphthol;
thiophenol; or
4-methylphenylthiol
for 2-methoxyphenol, the following epoxide compounds of formula A are obtained:
1-(2-methylphenoxy)-2,3-epoxypropane;
1-(3-methylphenoxy)-2,3-epoxypropane;
1-(4-methylphenoxy)-2,3-epoxypropane;
1-(4-n-butylphenoxy)-2,3-epoxypropane;
1-(2-methoxyphenoxy)-2,3-epoxypropane;
1-(4-methoxyphenoxy)-2,3-epoxypropane;
1-(2-isopropoxyphenoxy)-2,3-epoxypropane;
1-(2-n-butoxyphenoxy)-2,3-epoxypropane;
1-(2-chlorophenoxy)-2,3-epoxypropane;
1-(4-bromophenoxy)-2,3-epoxypropane;
1-(2,4-dimethylphenoxy)-2,3-epoxypropane;
1-(2,4-dichlorophenoxy)-2,3-epoxypropane;
1-(4-methyl-5-chlorophenoxy)-2,3-epoxypropane;

1-(3,4,5-trichlorophenoxy)-2,3-epoxypropane;
1-(3,4,5-trimethoxyphenoxy)-2,3-epoxypropane;
1-(3-methyl-4,5-dichlorophenoxy)-2,3-epoxypropane;
1-(3-methyl-4-chloro-5-methoxyphenoxy)-2,3-epoxypropane;
1-(2,3,4,5-tetrabromophenoxy)-2,3-epoxypropane;
1-(3,6-dimethyl-4,5-dichlorophenoxy)-2,3-epoxypropane;
1-(4-trifluoromethylphenoxy)-2,3-epoxypropane;
1-(4-methylthiophenoxy)-2,3-epoxypropane;
1-(4-n-butylthiophenoxy)-2,3-epoxypropane;
1-(4-methylsulfinylphenoxy)-2,3-epoxypropane;
1-(4-n-butylsulfinylphenoxy)-2,3-epoxypropane;
1-(4-methylsulfonylphenoxy)-2,3-epoxypropane;
1-(4-n-butylsulfonylphenoxy)-2,3-epoxypropane;
1-(2-cyanophenoxy)-2,3-epoxypropane;
1-(2-acetylphenoxy)-2,3-epoxypropane;
1-[(4-n-butanoylphenoxy)]-2,3-epoxypropane;
1-[4-(N,N-dimethylamino)phenoxy]-2,3-epoxypropane;
1-[4-(N,N-di-n-butylamino)phenoxy]-2,3-epoxypropane;
1-(1-naphthoxy)-2,3-epoxypropane;
1-(phenylthio)-2,3-epoxypropane; or
1-(4-methylphenylthio)-2,3-epoxypropane.

These compounds are of sufficient purity for use in Reaction Sequences 1 and 2.

(c) Similarly, proceeding as in Subpart (a) of this Preparation but substituting a stoichiometrically equivalent amount of S-epichlorohydrin for epichlorohydrin, there is obtained the R-1-(2-methoxyphenoxy)-2,3-epoxy-propane in good yield.

(d) Similarly, proceeding as in Subpart (c) of this Preparation but substituting a stoichiometrically equivalent amount of the substituted phenol cited for 2-methoxyphenol, the corresponding R-substituted phenoxy epoxide compounds of formula A are obtained.

(e) Similarly, proceeding in Subpart (a) of this Preparation but substituting a stoichiometrically equivalent amount of R-epichlorohydrin for epichlorohydrin, there is obtained the corresponding (S)-1-(2-methoxyphenoxy)-2,3-epoxypropane in good yield.

(f) Similarly, proceeding in Subpart (e) of this Preparation but substituting a stoichiometrically equivalent amount of R-epichlorohydrin for epichlorohydrin and a substituted phenol for 2-methoxyphenol, there is obtained a corresponding (S)-1-(substituted-phenoxy)-2,3-epoxypropane in good yield.

(g) Similarly proceeding in Subparts (a), (b), (c), (d), (e) or (f) above but substituting a stoichiometrically amount of an optionally substituted phenylthiol derivative for 2-methoxyphenol, there is obtained corresponding the R-, S- or R,S- 1-(optionally substituted-phenylthio)-2,3-epoxypropane.

PREPARATION B

Preparation of
[(2,6-dimethylphenyl)-aminocarbonylmethyl]chloride (Compound of formula F)

(a) 2,6-Dimethylaniline (96 g, 793 mmoles) and triethylamine (TEA) (96 g, 130 ml) are dissolved in one liter of methylene chloride. The mixture is cooled in ice, and the chloroacetyl chloride (89.6 g, 800 mmoles) is added slowly. The mixture is stirred for 4 hours and becomes very dark in color. The mixture is then washed with dilute hydrochloric acid, and concentrated under vacuum. Hexane is added to precipitate the product, [(2,6-dimethylphenyl)aminocarbonylmethyl]chloride, and the crude product is filtered, is washed and dried. A yield of 130 g is obtained, in sufficient purity for use in Reaction Sequences 1 or 2.

(b) Repeating the above procedure in a similar manner and substituting a stoichiometrically equivalent of:
aniline;
2-chloroaniline;
3-chloroaniline;
4-chloroaniline;
2-bromoaniline;
3-bromoaniline;
4-bromoaniline;
2-fluoroaniline;
3-fluoroaniline;
4-fluoroaniline;
2-methylaniline;
3-methylaniline;
4-methylaniline;
4-n-butylaniline;
2-methoxyaniline;
3-methoxyaniline;
4-methoxyaniline;
4-n-butoxyaniline;
2-trifluoromethylaniline;
3-trifluoromethylaniline;
4-trifluoromethylaniline;
2,6-dichloroaniline;
3,5-dimethoxyaniline;
3,4-methylenedioxyaniline;
2-chloro-5-methylaniline;
4-methylthioaniline;
4-methylsulfinylaniline;
4-methylsulfonylaniline;
4-n-butylthioaniline;
4-n-butylsulfinylaniline;
4-n-butylsulfonylaniline;
3,4-difluoroaniline;
4-chloro-3-trifluoromethylaniline;
4-fluoro-3-trifluoromethylaniline;
2,5-diethoxyaniline;
2,4,5-trichloroaniline;
3,4,5-trimethoxyaniline;
2,4,5,6-tetrachloroaniline;
2,3,4,6-tetramethylaniline;
2,3,4,5,6-pentachloroaniline;
3-chloro-2,4,6-trimethylaniline;
2-cyanoaniline;
4-(acetamido)aniline;
4-(N-methylacetamido)aniline;
4-(N-n-butylacetamido)aniline;
N-methylaniline;
N-n-butylaniline;
N-methyl-2,6-dimethylaniline; or
N-n-butyl-2,6-dimethylaniline
for 2,6-dimethylaniline, there are obtained the following substituted chlorides of formula F:
(phenylaminocarbonylmethyl)chloride;
[(2-chlorophenyl)aminocarbonylmethyl]chloride;
[(3-chlorophenyl)aminocarbonylmethyl]chloride;
[(4-chlorophenyl)aminocarbonylmethyl]chloride;
[(2-bromophenyl)aminocarbonylmethyl]chloride;
[(3-bromophenyl) aminocarbonylmethyl]chloride;
[(4-bromophenyl)aminocarbonylmethyl]chloride;
[(2-fluorophenyl)aminocarbonylmethyl]chloride;
[(3-fluorophenyl)aminocarbonylmethyl]chloride;
[(4-fluorophenyl)aminocarbonylmethyl]chloride;
[(2-methylphenyl)aminocarbonylmethyl]chloride;
[(3-methylphenyl)aminocarbonylmethyl]chloride;

[(4-methylphenyl)aminocarbonylmethyl]chloride;
[(4-n-butylphenyl)aminocarbonylmethyl]chloride;
[(2-methoxyphenyl)aminocarbonylmethyl]chloride;
[(3-methoxyphenyl)aminocarbonylmethyl]chloride;
[(4-methoxyphenyl)aminocarbonylmethyl]chloride;
[(4-n-butoxyphenyl)aminocarbonylmethyl]chloride;
[(2-trifluoromethylphenyl)aminocarbonylmethyl]chloride;
[(3-trifluoromethylphenyl)aminocarbonylmethyl]chloride;
[(4-trifluoromethylphenyl)aminocarbonylmethyl]chloride;
[(2,6-dichlorophenyl)aminocarbonylmethyl]chloride;
[(3,5-dimethoxyphenyl)aminocarbonylmethyl]chloride;
[(3,4-methylenedioxyphenyl)aminocarbonylmethyl]chloride;
[(2-chloro-5-methylphenyl)aminocarbonylmethyl]chloride;
[(4-methylthiophenyl)aminocarbonylmethyl]chloride;
[(4-methylsulfinylphenyl)aminocarbonylmethyl]chloride;
[(4-methylsulfonylphenyl)aminocarbonylmethyl]chloride;
[(4-n-butylthiophenyl)aminocarbonylmethyl]chloride;
[(4-n-butylsulfinylphenyl)aminocarbonylmethyl]chloride;
[(4-n-butylsulfonylphenyl)aminocarbonylmethyl]chloride;
[(3,4-difluorophenyl)aminocarbonylmethyl]chloride;
[(4-chloro-3-trifluoromethylphenyl)aminocarbonylmethyl]chloride;
[(4-fluoro-3-trifluoromethylphenyl)aminocarbonylmethyl]chloride;
[(2,5-diethoxyphenyl)aminocarbonylmethyl]chloride;
[(2,4,5-trichlorophenyl)aminocarbonylmethyl]chloride;
[(3,4,5-trimethoxyphenyl)aminocarbonylmethyl]chloride;
[(2,4,5,6-tetrachlorophenyl)aminocarbonylmethyl]chloride;
[(2,3,4,6-tetramethylphenyl)aminocarbonylmethyl]chloride;
[(2,3,4,5,6-pentachlorophenyl)aminocarbonylmethyl]chloride;
[(3-chloro-2,4,6-trimethylphenyl)aminocarbonylmethyl]chloride;
[(2-cyanophenyl)aminocarbonylmethyl]chloride;
[(4-acetamidophenyl)aminocarbonylmethyl]chloride;
[(4-N-methylacetamidophenyl)aminocarbonylmethyl]chloride;
[(4-N-n-butylacetamidophenyl)aminocarbonylmethyl]chloride;
[N-methyl-N-(phenyl)aminocarbonylmethyl]chloride;
[N-n-butyl-N-(phenyl)aminocarbonylmethyl]chloride;
[N-methyl-N-(2,6-dimethylphenyl)aminocarbonylmethyl]chloride; or
[N-n-butyl-N-(2,6-dimethylphenyl)aminocarbonylmethyl]chloride
of sufficient purity for use in Reaction Sequences 1 or 2.

(c) Repeating the above procedure in Subpart (a) in a similar manner and substituting a stoichiometrically equivalent amount of:
2-chloropropanoyl chloride;
2-chloro-n-butanoyl chloride; or
2-chloro-n-hexanoyl chloride
for chloroacetylchloride, there is obtained the following substituted chloride of formula F:
[(2,6-dimethylphenyl)aminocarbonyl-1-ethyl]chloride;
[(2,6-dimethylphenyl)aminocarbonyl)-1-n-propyl]chloride; or
[(2,6-dimethylphenyl)aminocarbonyl-1-n-pentyl]chloride.

(d) Repeating the above procedure in Subpart (a) in a similar manner and substituting a stoichiometrically equivalent amount of
aniline;
N-methyl-2,6-dimethylaniline; or
N-n-butyl-2,6-dimethylaniline
for 2,6-dimethylaniline and 2-chloropropanoyl chloride for chloroacetylchloride, there is obtained the corresponding
[phenylaminocarbonyl-1-ethyl]chloride;
[N-methyl-N-(2,6-dimethylphenyl)aminocarbonyl-1-ethyl]chloride; or
[N-n-butyl-N-(2,6-dimethylphenyl)aminocarbonyl-1-ethyl]chloride.

(e) Repeating the above procedure in Subpart (a) in a similar manner and substituting a stoichiometrically equivalent amount of
aniline;
N-methyl-2,6-dimethylaniline; or
N-n-butyl-2,6-dimethylaniline
for 2,6-dimethylaniline, and 2-chloro-n-hexanoyl chloride for chloroacetyl chloride, there is obtained the corresponding
[(phenyl)aminocarbonyl-1-n-pentyl]chloride;
[N-methyl-N-(2,6-dimethylphenyl)aminocarbonyl-1-n-pentyl]chloride; or
[N-n-butyl-N-(2,6-dimethylphenyl)aminocarbonyl-1-n-pentyl]chloride.

PREPARATION C

Preparation of 1-[(2,6-dimethylphenyl)aminocarbonylmethyl]piperazine (Compound of formula G)

(a) The crude [(2,6-dimethylphenyl)aminocarbonylmethyl]chloride, prepared in Preparation B (50 g, 0.25 mole) and piperazine (86 g, 1 mole) are dissolved in 500 ml of ethanol. The mixture is refluxed for two hours, and then cooled and evaporated. The product is harvested by adding aqueous ammonia to the residue, and extracting with methylene chloride. Three portions of methylene chloride are used, which are collected, washed with water, and evaporated to a semi-solid. Upon addition of ether, the product crystallizes and is filtered. The resulting crude mixture is boiled with ether and then evaporated to a residue and triturated with hexane to yield pure material, 1-[(2,6-dimethylphenyl)aminocarbonylmethyl]piperazine. This material is of sufficient purity for use in Reaction Sequences 1 or 2.

(b) Repeating the above procedure [Subpart (a)] in a similar manner and substituting a stoichiometrically equivalent of:
phenylaminocarbonylmethylchloride;
[(4-chlorophenyl)aminocarbonylmethyl]chloride;
[(4-methylphenyl)aminocarbonylmethyl]chloride;
[(4-methoxyphenyl)aminocarbonylmethyl]chloride;
[(3-chlorophenyl)aminocarbonylmethyl]chloride;
[(2,6-dichlorophenyl)aminocarbonylmethyl]chloride;
[(2,4,6-trimethylphenyl)aminocarbonylmethyl]chloride;
[(3,5-dimethoxyphenyl)aminocarbonylmethyl]chloride;
[(4-methylthiophenyl)aminocarbonylmethyl]chloride;
[(4-n-butylthiophenyl)aminocarbonylmethyl]chloride;

[(4-methylsulfinylphenyl)aminocarbonylmethyl]chloride;
[(4-n-butylsulfinylphenyl)aminocarbonylmethyl]chloride;
[(4-methylsulfonylphenyl)aminocarbonylmethyl]chloride;
[(4-n-butylsulfonylphenyl)aminocarbonylmethyl]chloride;
[(4-trifluoromethylphenyl)aminocarbonylmethyl]chloride;
[(2-chloro-5-methylphenyl)aminocarbonylmethyl]chloride;
[(3,5-difluorophenyl)aminocarbonylmethyl]chloride;
[(4-chloro-3-trifluoromethylphenyl)aminocarbonylmethyl]chloride;
[(4-fluoro-3-trifluoromethylphenyl)aminocarbonylmethyl]chloride;
[(2,6-diethoxyphenyl)aminocarbonylmethyl]chloride;
[(3-bromo-4-ethylphenyl)aminocarbonylmethyl]chloride;
[(4-n-butylphenyl)aminocarbonylmethyl]chloride;
[(4-isobutylphenyl)aminocarbonylmethyl]chloride;
[(3,4,5-trimethoxyphenyl)aminocarbonylmethyl]chloride;
[(2,3,4,5-tetrachlorophenyl)aminocarbonylmethyl]chloride;
[(2,3,4,5,6-pentachlorophenyl)aminocarbonylmethyl]chloride;
[(2-cyanophenyl)aminocarbonylmethyl]chloride;
[(4-acetamidophenyl)aminocarbonylmethyl]chloride;
[(4-N-methylacetamidophenyl)aminocarbonylmethyl]chloride;
[(4-N-n-butylacetamidophenyl)aminocarbonylmethyl]chloride;
[N-methyl-N-(phenyl)aminocarbonylmethyl]chloride;
[N-n-butyl-N-(phenyl)aminocarbonylmethyl]chloride;
[N-methyl-N-(2,6-dimethylphenyl)aminocarbonylmethyl]chloride;
[N-n-butyl-N-(2,6-dimethylphenyl)aminocarbonylmethyl]chloride;
[(2,6-dimethylphenyl)aminocarbonyl-1-ethyl]chloride;
[N-methyl-N-(2,6-dimethylphenyl)aminocarbonyl-1-ethyl]chloride;
[N-methyl-N-(2,6-dimethylphenyl)aminocarbonyl-1-ethyl]chloride;
[N-n-butyl-N-(2,6-dimethylphenyl)aminocarbonyl-1-ethyl]chloride;
[(2,6-dimethylphenyl)aminocarbonyl-1-n-pentyl]chloride;
[N-methyl-N-(2,6-dimethylphenyl)aminocarbonyl-1-n-pentyl]chloride; or
[N-n-butyl-N-(2,6-dimethylphenyl)aminocarbonyl-1-n-pentyl]chloride
for [(2,6-dimethylphenyl)aminocarbonylmethyl]chloride, there are obtained the following piperazines:
1-(phenylaminocarbonylmethyl)piperazine;
1-[(4-chlorophenyl)aminocarbonylmethyl]piperazine;
1-[(4-methylphenyl)aminocarbonylmethyl]piperazine;
1-[(4-methoxyphenyl)aminocarbonylmethyl]piperazine;
1-[(3-chlorophenyl)aminocarbonylmethyl]piperazine;
1-[(2,6-dichlorophenyl)aminocarbonylmethyl]piperazine;
1-[(2,4,6-trimethylphenyl)aminocarbonylmethyl]piperazine;
1-[(3,5-dimethoxyphenyl)aminocarbonylmethyl]piperazine;
1-[(4-methylthiophenyl)aminocarbonylmethyl]piperazine;
1-[(4-n-butylthiophenyl)aminocarbonylmethyl]piperazine;
1-[(4-methylsulfinylphenyl)aminocarbonylmethyl]piperazine;
1-[(4-n-butylsulfinylphenyl)aminocarbonylmethyl]piperazine;
1-[(4-methylsulfonylphenyl)aminocarbonylmethyl]piperazine;
1-[(4-n-butylsulfonylphenyl)aminocarbonylmethyl]piperazine;
1-[(4-trifluoromethylphenyl)aminocarbonylmethyl]piperazine;
1-[(2-chloro-5-methylphenyl)aminocarbonylmethyl]piperazine;
1-[(3,5-difluorophenyl)aminocarbonylmethyl]piperazine;
1-[(4-chloro-3-trifluoromethylphenyl)aminocarbonylmethyl]piperazine;
1-[(4-fluoro-3-trifluoromethylphenyl)aminocarbonylmethyl]piperazine;
1-[(2,6-diethoxyphenyl)aminocarbonylmethyl]piperazine;
1-[(3-bromo-4-ethylphenyl)aminocarbonylmethyl]piperazine;
1-[(4-n-butylphenyl)aminocarbonylmethyl]piperazine;
1-[(4-isobutylphenyl)aminocarbonylmethyl]piperazine;
1-[(3,4,5-trimethoxyphenyl)aminocarbonylmethyl]piperazine;
1-[(2,3,4,5-tetrachlorophenyl)aminocarbonylmethyl]piperazine;
1-[(2,3,4,5,6-pentachlorophenyl)aminocarbonylmethyl]piperazine;
[(2-cyanophenyl)aminocarbonylmethyl]piperazine;
[(4-acetamidophenyl)aminocarbonylmethyl]piperazine;
[(4-N-methylacetamidophenyl)aminocarbonylmethyl]piperazine;
[(4-N-n-butylacetamidophenyl)aminocarbonylmethyl]piperazine;
1-[N-methyl-N-(phenyl)aminocarbonylmethyl]piperazine;
1-[N-n-butyl-N-(phenyl)aminocarbonylmethyl]piperazine;
1-[N-methyl-N-(2,6-dimethylphenyl)aminocarbonylmethyl]piperazine;
1-[N-n-butyl-N-(2,6-dimethylphenyl)aminocarbonylmethyl]piperazine;
[(2,6-dimethylphenyl)aminocarbonyl-1-ethyl]piperazine;
[N-methyl-N-(2,6-dimethylphenyl)aminocarbonyl-1-ethyl]piperazine;
[N-methyl-N-(2,6-dimethylphenyl)aminocarbonyl-1-ethyl]piperazine;
[N-n-butyl-N-(2,6-dimethylphenyl)aminocarbonyl-1-ethyl]piperazine;
[(2,6-dimethylphenyl)aminocarbonyl-1-n-pentyl]piperazine;
[N-methyl-N-(2,6-dimethylphenyl)aminocarbonyl-1-n-pentyl]piperazine; or
[N-n-butyl-N-(2,6-dimethylphenyl)aminocarbonyl-1-n-pentyl]piperazine in sufficient purity for use in Reaction Sequences 1 and 2.

PREPARATION D

Preparation of
1-[3-(2-methoxyphenoxy)-2-hydroxypropyl]piperazine (Compound of formula E)

(a) In a manner similar to that described in Subpart (a) of Preparation C, but substituting 2-(2-methoxyphenoxy)-2,3-epoxypropane for the starting chloride and maintaining at ambient temperature for two days, one obtains the corresponding compound of formula E, namely, 1-[3-(2-methoxyphenoxy)-2-hydroxypropyl]-piperazine.

(b) Repeating the above procedure [Subpart (a)] in a similar manner and substituting a stoichiometrically equivalent amount of:

1-(2-methylphenoxy)-2,3-epoxypropane;
1-(2-methoxyphenoxy)-2,3-epoxypropane;
1-(2-chlorophenoxy)-2,3-epoxypropane;
1-(2-bromophenoxy)-2,3-epoxypropane;
1-(4-methylphenoxy)-2,3-epoxypropane;
1-(4-methoxyphenoxy)-2,3-epoxypropane;
1-(2-isopropoxyphenoxy)-2,3-epoxypropane;
1-(2-n-butoxyphenoxy)-2,3-epoxypropane;
1-(4-chlorophenoxy)-2,3-epoxypropane;
1-(2,4-dimethylphenoxy)-2,3-epoxypropane;
1-(2,4-dichlorophenoxy)-2,3-epoxypropane;
1-(3,4,5-trichlorophenoxy)-2,3-epoxypropane;
1-(3,4,5-trimethoxyphenoxy)-2,3-epoxypropane;
1-(3-methyl-4-chloro-5-methoxyphenoxy)-2,3-epoxypropane;
1-(2,3,4,5-tetrabromophenoxy)-2,3-epoxypropane;
1-(2,6-dimethyl-3,4-dichlorophenoxy)-2,3-epoxypropane;
1-(4-trifluoromethylphenoxy)-2,3-epoxypropane;
1-(4-methylthiophenoxy)-2,3-epoxypropane;
1-(4-methylsulfinylphenoxy)-2,3-epoxypropane;
1-(4-methylsulfonylphenoxy)-2,3-epoxypropane;
1-(4-n-butylthiophenoxy)-2,3-epoxypropane;
1-(4-n-butylsulfinylphenoxy)-2,3-epoxypropane;
1-(4-n-butylsulfonylphenoxy)-2,3-epoxypropane;
1-(2-acetylphenoxy)-2,3-epoxypropane;
1-(4-n-butanoylphenoxy)-2,3-epoxypropane;
1-(4-aminocarbonylmethylphenoxy)-2,3-epoxypropane;
1-(4-N,N-dimethylaminophenoxy)-2,3-epoxypropane;
1-(4-N,N-di-n-butylaminophenoxy)-2,3-epoxypropane;
1-(1-naphthoxy)-2,3-epoxypropane
1-(phenylthio)-2,3-epoxypropane; or
1-(4-methylphenylthio)-2,3-epoxypropane for 1-[(2,6-dimethylphenyl)aminocarbonylmethyl]chloride, there are obtained the following piperazines:

1-[3-(2-methylphenoxy)-2-hydroxypropyl]piperazine;
1-[3-(2-methoxyphenoxy)-2-hydroxypropyl]piperazine;
1-[3-(2-chlorophenoxy)-2-hydroxypropyl]piperazine;
1-[3-(2-bromophenoxy)-2-hydroxypropyl]piperazine;
1-[3-(4-methylphenoxy)-2-hydroxypropyl]piperazine;
1-[3-(4-methoxyphenoxy)-2-hydroxypropyl]piperazine;
1-[3-(2-isopropoxyphenoxy)-2-hydroxypropyl]piperazine;
1-[3-(2-n-butoxyphenoxy)-2-hydroxypropyl]piperazine;
1-[3-4-chlorophenoxy)-2-hydroxypropyl]piperazine;
1-[3-(2,4-dimethylphenoxy)-2-hydroxypropyl]piperazine;
1-[3-(2,4-dichlorophenoxy)-2-hydroxypropyl]piperazine;
1-[3-(3,4,5-trichlorophenoxy)-2-hydroxypropyl]piperazine;
1-[3-(3,4,5-trimethoxyphenoxy)-2-hydroxypropyl]piperazine;
1-[3-(3-methyl-4-chloro-5-methoxyphenoxy)-2-hydroxypropyl]piperazine;
1-[3-(2,3,4,5-tetrabromophenoxy)-2-hydroxypropyl]piperazine;
1-[3-(2,6-dimethyl-3,4-dichlorophenoxy)-2-hydroxypropyl]piperazine;
1-[3-(4-trifluoromethylphenoxy)-2-hydroxypropyl]piperazine;
1-[3-(4-methylthiophenoxy)-2-hydroxypropyl]piperazine;
1-[3-(4-methylsulfinylphenoxy)-2-hydroxypropyl]piperazine;
1-[3-(4-methylsulfonylphenoxy)-2-hydroxypropyl]piperazine;
1-[3-(4-n-butylthiophenoxy)-2-hydroxypropyl]piperazine;
1-[3-(4-n-butylsulfinylphenoxy)-2-hydroxypropyl]piperazine;
1-[3-(4-n-butylsulfonylphenoxy)-2-hydroxypropyl]piperazine.
1-[3-(2-acetylphenoxy)-2-hydroxypropyl]piperazine;
1-[3-(4-n-butanoylphenoxy)-2-hydroxypropyl]piperazine;
1-[3-(4-aminocarbonylmethylphenoxy)-2-hydroxypropyl]piperazine;
1-[3-(4-N,N-dimethylaminophenoxy)-2-hydroxypropyl]piperazine;
1-[3-(4-N,N-di-n-butylaminophenoxy)-2-hydroxypropyl]piperazine;
1-[3-(1-naphthoxy)-2-hydroxypropyl]piperazine;
1-[3-(phenylthio)-2-hydroxypropyl]piperazine; or
1-[3-(4-methylphenylthio)-2-hydroxypropyl]piperazine.

(c) Repeating the above procedure [Subpart (a)] in a similar manner and substituting a stoichiometrically equivalent amount of R-3-(2-methoxyphenoxy)-2,3-epoxide for 3-(2-methoxyphenoxy)-2,3-epoxide, one obtains the corresponding R-1-[3-(2-methoxyphenoxy)-2-hydroxypropyl]piperazine.

(d) Repeating the above procedure [Subpart (a)] in a similar manner and substituting a stoichiometrically equivalent amount of one of the R-substituted phenoxy-2,3-epoxides named of Preparation A [Subpart (b)] for 1-(2-methoxyphenoxy)-2,3-epoxypropane, one obtains the corresponding R-[3-(substituted-phenoxy)-2-hydroxypropyl]piperazine.

(e) Repeating the above procedure [Subpart (a)] in a similar manner and substituting a stoichiometrically equivalent of S-1-(2-methoxyphenoxy)-2,3-epoxypropane for 1-(2-methoxyphenoxy)-2,3-epoxypropane, one obtains the corresponding S-1-[3-(2-methoxyphenoxy)-2-hydroxypropyl]piperazine.

(f) Repeating the above procedure [Subpart (a)] in a similar manner and substituting a stoichiometrically equivalent of any one of the S-1-(substituted phenoxy)-2,3-epoxypropanes in Preparation A [Subpart (d)] for 1-(substituted phenoxy)-2,3-epoxpropane, one obtains the corresponding S-1-(substituted-phenoxy)-2-hydroxypropyl]piperazine.

(g) Repeating the above procedure [Subpart (a)] in a similar manner and substituting a stoichiometrically equivalent amount of a mixture of any one of the R- and S-unsubstituted or aryl substituted-phenoxy-2,3-epoxides of Preparation A [Subparts (e) or (f)] for 1-(2-methoxyphenoxy)-2,3-epoxypropane, one obtains the corresponding mixture of R- and S-unsubstituted or aryl substituted-phenoxy-2-hydroxypropyl]piperazine.

EXAMPLE 1

Preparation of
1-[3-(2-Methoxyphenoxy)-2-hydroxypropyl]-4-[(2,6-dimethylphenyl)aminocarbonylmethyl]piperazine (Reaction Sequence 1)

(a) The [(2,6-dimethylphenyl)aminocarbonylmethyl]-chloride from Preparation B [Subpart (a)] (12.9 g, 65 mmoles) and 1-[3-(2-methoxyphenoxy)-2-hydroxypropyl]piperazine from Preparation D [Subpart (a)] (15 g, 65 mmoles) are mixed in 100 ml of dimethylformamide. The mixture is stirred at 65° C. to dissolve the components, and then at 90° C. overnight. The entire mixture is added to water and acidified with hydrochloric acid. The resulting homogeneous mixture is washed with ether, and then made basic with ammonia, and extracted with three portions of methylene chloride. The methylene chloride extracts, which contained the product, are washed with water twice, and then evaporated to 28 g of an oil. The oil is purified by chromatographing with 500 g of silica gel with 5% methanol in methylene chloride. The 20 g of yellow oil which are obtained were dissolved in methanol and crystallized by the addition of hydrochloric acid. Precipitation is completed by addition of ether and 16 g of the product, 1-[3-(2-methoxyphenoxy)-2-hydroxypropyl]-4-[(2,6-dimethylphenyl)aminocarbonylmethyl]piperazine, is obtained as an oil.

Because the 1-[3-(2-methoxyphenoxy)-2-hydroxypropyl]piperazine from Preparation D has undefined stereochemistry at the carbon atom at the 2 chain position, this compound and the substituted compounds of Subparts (b), (c) and (d) below are obtained as a mixture of the R- and S- isomers.

(b) Similarly, proceeding as in Subpart (a) above but substituting a stoichiometrically equivalent amount of any one of the substituted chloride compounds prepared in Preparation C above for 1-[(2,6-dimethylphenyl)aminocarbonylmethyl]chloride, there is obtained the corresponding 1-[3-(2-methoxyphenoxy)-2-hydroxypropyl]-4-[(substituted-phenyl)aminocarbonylmethyl]piperazine.

Exemplary compounds are as follows:

1-[3-(2-methoxyphenoxy)-2-hydroxypropyl]-4-(phenylaminocarbonylmethyl)piperazine;

1-[3-(2-methoxyphenoxy)-2-hydroxypropyl]-4-[4-(chlorophenyl)aminocarbonylmethyl]piperazine;

1-[3-(2-methoxyphenoxy)-2-hydroxypropyl]-4-[(4-methylphenyl)aminocarbonylmethyl]piperazine;

1-[3-(2-methoxyphenoxy)-2-hydroxypropyl]-4-[(4-methoxyphenyl)aminocarbonylmethyl]piperazine;

1-[3-(2-methoxyphenoxy)-2-hydroxypropyl]-4-[(4-bromophenyl)aminocarbonylmethyl]piperazine;

1-[3-(2-methoxyphenoxy)-2-hydroxypropyl]-4-[(3-(chlorophenyl)aminocarbonylmethyl]piperazine;

1-[3-(2-methoxyphenoxy)-2-hydroxypropyl]-4-[(2,6-dichlorophenyl)aminocarbonylmethyl]piperazine;

1-[3-(2-methoxyphenoxy)-2-hydroxypropyl]-4-[(2,4,6-trimethylphenyl)aminocarbonylmethyl]piperazine;

1-[3-(2-methoxyphenoxy)-2-hydroxypropyl]-4-[(3,4,5-dimethoxyphenyl)aminocarbonylmethyl]piperazine;

1-[3-(2-methoxyphenoxy)-2-hydroxypropyl]-4-[(4-methylthiophenyl)aminocarbonylmethyl]piperazine;

1-[3-(2-methoxyphenoxy)-2-hydroxypropyl]-4-[(4-ethylthiophenyl)aminocarbonylmethyl]piperazine;

1-[3-(2-methoxyphenoxy)-2-hydroxypropyl]-4-[(4-methylsulfinylphenyl)aminocarbonylmethyl]piperazine;

1-[3-(2-methoxyphenoxy)-2-hydroxypropyl]-4-[(4-n-propylsulfinylphenyl)aminocarbonylmethyl]piperazine;

1-[3-(2-methoxyphenoxy)-2-hydroxypropyl]-4-[(4-trifluoromethylphenyl)aminocarbonylmethyl]piperazine;

1-[3-(2-methoxyphenoxy)-2-hydroxypropyl]-4-[(2-chloro-5-methylphenyl)aminocarbonylmethyl]-piperazine;

1-[3-(2-methoxyphenoxy)-2-hydroxypropyl]-4-[(3,5-difluorophenyl)aminocarbonylmethyl]piperazine;

1-[3-(2-methoxyphenoxy)-2-hydroxypropyl]-4-[(2,6-diethoxyphenyl)aminocarbonylmethyl]piperazine;

1-[3-(2-methoxyphenoxy)-2-hydroxypropyl]-4-[(3-bromo-4-ethylphenyl)aminocarbonylmethyl]piperazine;

1-[3-(2-methoxyphenoxy)-2-hydroxypropyl]-4-[(4-n-butylphenyl)aminocarbonylmethyl]piperazine; and 1-[3-(2-methoxyphenoxy)-2-hydroxypropyl]-4-[(4-isobutylphenyl)aminocarbonylmethyl]piperazine.

(c) Similarly, proceeding as in Subpart (a) above but substituting a stoichiometrically equivalent amount of any one of the substituted piperazine compounds described in Preparation D [Subpart (b)] above for 2-[(phenoxy)-2-hydroxypropyl]piperazine, there is obtained the corresponding 1-[3-(substituted-phenoxy)-2-hydroxypropyl]-4-[(2,6-dimethylphenyl)aminocarbonylmethyl]piperazine.

Exemplary compounds include the following:

1-[3-(4-methylphenoxy)-2-hydroxypropyl]-4-[(2,6-dimethylphenyl)aminocarbonylmethyl]piperazine;

1-[3-(4-methoxyphenoxy)-2-hydroxypropyl]-4-[(2,6-dimethylphenyl)aminocarbonylmethyl]piperazine;

1-[3-(4-chlorophenoxy)-2-hydroxypropyl]-4-[(2,6-dimethylphenyl)aminocarbonylmethyl]piperazine;

1-[3-(3-methylphenoxy)-2-hydroxypropyl]-4-[(2,6-dimethylphenyl)aminocarbonylmethyl]piperazine;

1-[3-(3-methoxyphenoxy)-2-hydroxypropyl]-4-[(2,6-dimethylphenyl)aminocarbonylmethyl]piperazine;

1-[3-(3-chlorophenoxy)-2-hydroxypropyl]-4-[(2,6-dimethylphenyl)aminocarbonylmethyl]piperazine;

1-[3-(2,4-dimethylphenoxy)-2-hydroxypropyl]-4-[(2,6-dimethylphenyl)aminocarbonylmethyl]piperazine;

1-[3-(2-acetylphenoxy)-2-hydroxypropyl]-4-[(2,6-dimethylphenyl)aminocarbonylmethyl]piperazine;

1-[3-(4-aminocarbonylmethylphenoxy)-2-hydroxypropyl]-4-[(2,6-dimethylphenyl)aminocarbonylmethyl]piperazine; or 1-[3-(1-naphthoxy)-2-hydroxypropyl]-4-[(2,6-dimethylphenyl)aminocarbonylmethyl]piperazine.

(d) Similarly, proceeding as in [Subpart (a)] above but substituting a stoichiometrically equivalent amount of any one of the substituted chloride compounds described in Preparation B above for 1-[(2,6-dimethylphenyl)aminocarbonylmethyl]chloride and also substituting a stoichiometrically equivalent amount of any one of the substituted piperazine compounds described in Preparation D [(Subpart (b)] above for 1-[3-(2-methoxyphenoxy)-2-hydroxypropyl]piperazine, there is obtained the corresponding 1-[3-(substituted-phenoxy-2-hydroxypropyl)]-4-[(substituted-phenyl)aminocarbonylalkyl]piperazine.

Exemplary compounds are as follows:

1-[3-(4-methylphenoxy)-2-hydroxypropyl]-4-(phenylaminocarbonylmethyl)piperazine;

1-[3-(4-chlorophenoxy)-2-hydroxypropyl]-4-[(4-chlorophenyl)aminocarbonylmethyl]piperazine;

1-[3-(3-methylphenoxy)-2-hydroxypropyl]-4-[(4-methylphenyl)aminocarbonylmethyl]piperazine;

1-[3-(4-methoxyphenoxy)-2-hydroxypropyl]-4-[(4-methoxyphenyl)aminocarbonylmethyl]piperazine;

1-[3-(2,4-dimethylphenoxy)-2-hydroxypropyl]-4-[(4-chlorophenyl)aminocarbonylmethyl]piperazine;

1-[3-(3-methoxyphenoxy)-2-hydroxypropyl]-4-[(3-chlorophenyl)aminocarbonylmethyl]piperazine;

1-[3-(4-methoxyphenoxy)-2-hydroxypropyl]-4-[(2,6-dichlorophenyl)aminocarbonylmethyl]piperazine;

1-[3-(4-methoxyphenoxy)-2-hydroxypropyl]-4-[(2,4,6-trimethylphenyl)aminocarbonylmethyl]piperazine;

1-[3-(4-methylthiophenoxy)-2-hydroxypropyl]-4-[(3,5-dimethoxyphenyl)aminocarbonylmethyl]piperazine;

1-[3-(2-chlorophenoxy)-2-hydroxypropyl]-4-[(4-methylthiophenyl)aminocarbonylmethyl]piperazine;

1-[3-(2-methylphenoxy)-2-hydroxypropyl]-4-[(4-ethylthiophenyl)aminocarbonylmethyl]piperazine;

1-[3-(2-methoxyphenoxy)-2-hydroxypropyl]-4-[4-methylsulfinylphenyl)aminocarbonylmethyl]piperazine;

1-[3-(4-trifluoromethylphenoxy)-2-hydroxypropyl]-4-[(4-n-butylsulfinylphenyl)aminocarbonylmethyl]piperazine;

1-[3-(2-methylphenoxy)-2-hydroxypropyl]-4-[(4-trifluoromethylphenyl)aminocarbonylmethyl]piperazine;

1-[3-(2-methylsulfinylphenoxy)-2-hydroxypropyl]-4-[(2-chloro-5-methylphenyl)aminocarbonylmethyl]piperazine;

1-[3-(4-methylsulfonylphenoxy)-2-hydroxypropyl]-4-[(3,5-difluorophenyl)aminocarbonylmethyl]-piperazine;

1-[3-(4-n-butylsulfinylphenoxy)-2-hydroxypropyl]-4-[(2,6-diethoxyphenyl)aminocarbonylmethyl]-piperazine;

1-[3-(4-methoxyphenoxy)-2-hydroxypropyl]-4-[(3-bromo-4-ethylphenyl)aminocarbonylmethyl]piperazine;

1-[3-(4-methylthiophenoxy)-2-hydroxypropyl]-4-[(4-n-butylphenyl)aminocarbonylmethyl]piperazine;

1-[3-(3-methoxyphenoxy)-2-hydroxypropyl]-4-[(4-isobutylphenyl)aminocarbonylmethyl]piperazine;

1-[3-(4-n-butylthiophenoxy)-2-hydroxypropyl]-4-[(2,6-dimethylphenyl)aminocarbonylmethyl]piperazine;

1-[3-(2-methyl-3,4-dichlorophenoxy)2-hydroxypropyl]-4-[(2,6-dimethylphenyl)aminocarbonylmethyl]piperazine;

1-[3-(2,3,4,5-tetrachlorophenoxy)2-hydroxypropyl]-4-[(2,6-dimethylphenyl)aminocarbonylmethyl]piperazine;

1-[3-(2-methyl-5-chlorophenoxy)2-hydroxypropyl]-4-[(2,6-dimethylphenyl)aminocarbonylmethyl]piperazine;

1-[3-(4-n-butylsulfinylphenoxy)-2-hydroxypropyl]-4-[(2,6-dimethylphenyl)aminocarbonylmethyl]piperazine;

1-[3-(4-n-butylsulfonylphenoxy)-2-hydroxypropyl]-4-[(2,6-dimethylphenyl)aminocarbonylmethyl]piperazine;

1-[3-(2,4-dimethylphenoxy)-2-hydroxypropyl]-4-[(2,6-dimethylphenyl)aminocarbonylmethyl]piperazine;

1-[3-(1-naphthoxy)-2-hydroxypropyl]-4-[(2,6-dimethylphenyl)aminocarbonylmethylpiperazine;

1-[3-(2-methoxyphenoxy)-2-hydroxypropyl]-4-[(2,6-dimethylphenyl)aminocarbonyl-1-ethyl]piperazine;

1-[3-(2-methoxyphenoxy)-2-hydroxypropyl]-4-[N-methyl-N-(2,6-dimethylphenyl)aminocarbonyl-1-ethyl]piperazine;

1-[3-(2-methoxyphenoxy)-2-hydroxypropyl]-4-[N-n-butyl-N-[(2,6-dimethylphenyl)aminocarbonyl-1-ethyl]piperazine;

1-[3-(2-methoxyphenoxy)-2-hydroxypropyl]-4-[(2,6-dimethylphenyl)aminocarbonyl-1-n-pentyl]piperazine;

1-[3-(2-methoxyphenoxy)-2-hydroxypropyl]-4-[N-methyl-N-[(2,6-dimethylphenyl)aminocarbonyl-1-n-pentyl]piperazine;

1-[3-(2-methoxyphenoxy)-2-hydroxypropyl]-4-[N-n-butyl-N-[(2,6-dimethylphenyl)aminocarbonyl-1-n-pentyl]piperazine;

1-[3-(phenylthio)-2-hydroxypropyl]-4-[(phenyl)aminocarbonylmethyl]piperazine; or 1-[3-(4-methylphenylthio)-2-hydroxypropyl]-4-[(phenylaminocarbonylmethyl]piperazine.

(e) Similarly, proceeding as in Subpart (a) above but substituting a stoichiometrically equivalent of R- or any one of the substituted R-1-phenoxy-2-hydroxypropyl]-piperazine compounds described above in Preparation D [Subpart (d)] for 1-[(3-(2-methoxyphenoxy)-2-hydroxypropyl]piperazine, and also substituting a stoichiometrically equivalent of any one of the substituted phenyl aminocarbonylmethyl chloride compounds described in Preparation B above for 1-[(2,6-dimethylphenyl)aminocarbonylmethyl]chloride, there is obtained the corresponding R-1-[3-(substituted-phenoxy-2-hydroxypropyl]-4-[(substituted phenyl)aminocarbonylmethyl]piperazine.

(f) Similarly, proceeding as in Subpart (a) above, but substituting the appropriately substituted R-isomer piperazine for 1-[3-(2-methoxyphenoxy)-2-hydroxypropyl]-piperazine, the following compounds having the R-configuration are prepared:

1-[3-(2-methylphenoxy)-2-hydroxypropyl]-4-[2,6-dimethylphenyl)aminocarbonylmethyl]piperazine;

1-[3-(2-methoxyphenoxy)-2-hydroxypropyl]-4-[2,6-dimethylphenyl)aminocarbonylmethyl]piperazine;

1-[3-(2-chlorophenoxy)-2-hydroxypropyl]-4-[2,6-dimethylphenyl)aminocarbonylmethyl]piperazine;

1-[3-(3-methylphenoxy)-2-hydroxypropyl]-4-[2,6-dimethylphenyl)aminocarbonylmethyl]piperazine;

1-[3-(3-methoxyphenoxy)-2-hydroxypropyl]-4-[2,6-dimethylphenyl)aminocarbonylmethyl]piperazine;

1-[3-(3-chlorophenoxy)-2-hydroxypropyl]-4-[(2,6-dimethylphenyl)aminocarbonylmethyl]piperazine; and 1-[3-(2,4-dimethylphenoxy)-2-hydroxypropyl]-4-[(2,6-dimethylphenyl)aminocarbonylmethyl]piperazine.

Additional exemplary compounds which may have the R-form are named in Subparts (b), (c), (d) and (e) of this example.

(g) Similarly, proceeding as in Subpart (a) above substituting a stoichiometrically equivalent amount of S-isomer or any one of the substituted S- isomers of 3-(substituted-phenoxy)-2-hydroxypropyl]piperazine compounds described in Preparation D [Subpart (f)] for 1-[3-(2-methoxyphenoxy)-2-hydroxypropyl]piperazine and also substituting a stoichiometrically equivalent amount of any one of the substituted phenyl aminocarbonylmethyl chloride compounds described in Preparation B [Subpart (b)] above for 1-[(2,6-dimethylphenyl)aminocarbonylmethyl]chloride, there is obtained the corresponding S-1-[3-(substituted-phenoxy)-2-hydroxypropyl]-4-(substituted-phenyl)aminocarbonylmethyl]-piperazine.

Additional exemplary compounds which may have the R- and S- forms as a mixture are named in Subparts (b), (c), (d), (e), and (f) of this example.

(h) Similarly, proceeding as in Subpart (a) above substituting a stoichiometrically equivalent amount of a mixture of R- and S- isomers or any one of the substituted R- and S- 1-[3-(substituted-phenoxy)-2-hydroxypropyl] piperazine compounds described in Preparation D [Subpart (g)] for 1-[3-(2-methoxyphenoxy)-2-hydroxypropyl]piperazine and also substituting a stoichiometrically equivalent of any one of the substituted phenyl aminocarbonylmethyl chloride compounds described in Preparation B [Subpart (b)] above for 1-[(2,6-dimethylphenyl)aminocarbonylmethyl]chloride, there is obtained the corresponding mixture of R- and S-1-[3-(substituted phenoxy-2-hydroxypropyl]-4-(substituted-phenyl)aminocarbonylmethyl]piperazine.

Additional exemplary compounds which may have the R- and S- forms as a mixture are named in Subparts (b), (c), (d), (e), and (f) of this example.

EXAMPLE 2

Preparation of 1-[3-(2-methoxyphenoxy) -2-hydroxypropyl]-4-[(2,6-dimethylphenyl)aminocarbonylmethyl]piperazine (Reaction Sequence 2)

(a) 1-(2-Methoxyphenoxy)-2,3-epoxypropane (2.0 g) from Preparation A and 4-[(2,6-dimethylphenyl)aminocarbonylmethyl]piperazine (2.5 g) were dissolved in 20 ml of methanol and 40 ml of toluene. The solution was refluxed for 5 hours evaporated and chromatographed on silica gel using 5% methanol/methylene chloride as eluent. Excess hydrochloric acid in methanol was added and the dihydrochloride salt was formed and recovered from methanol/ether as a white powder, 3 g, mp 164°–166° C.

Anal. for $C_{24}H_{35}N_3O_4Cl_2$; Calcd: C, 57.60; H, 7.05; N, 8.39. Found: C, 57.32; H, 7.19; N, 8.38.

Because the 1-(2-methoxyphenoxy)-2,3-epoxypropane from Preparation A [Subpart (a)] has undefined stereochemistry at the carbon atom at position 2 of the ring, this compound and the substituted compounds of Subparts (b), (c) and (d) below are obtained as a mixture of the R- and S- forms.

(b) Similarly, proceeding as in Subpart (a) above but substituting a stoichiometrically equivalent amount of any one of the substituted phenyl piperazine compounds described in Preparation B above for 1-[(2,6-dimethylphenyl)aminocarbonylmethyl]piperazine, there is obtained the corresponding 1-[3-(2-methoxyphenoxy)-2-hydroxypropyl]-4-[(substituted phenyl)aminocarbonylmethyl]piperazine.

Exemplary compounds are named in Example 1 [Subpart (b)] above.

(c) Similarly, proceeding as in Subpart (a) above but substituting stoichiometrically equivalent amount of any one of the substituted phenoxy epoxide compounds described in Preparation A, [Subpart (b)] above for epoxide, there is obtained the corresponding 1-[3-(substituted-phenoxy)-2-hydroxypropyl]-4-[(2,6-dimethylphenyl)aminocarbonylmethyl]piperazine.

Exemplary compounds are named in Example 1 above.

(d) Similarly, proceeding as in Subpart (a) above but substituting a stoichiometrically equivalent of any one of the substituted phenyl piperazine compounds described in Preparation C above for 1-[(2,6-dimethylphenyl)aminocarbonylmethyl]piperazine, and substituting a stoichiometrically equivalent of any one of the substituted phenoxy epoxides described in Preparation A above for 1-(2-methoxyphenoxy)-2,3-epoxypropane, there is obtained the corresponding 1-[3-(substituted phenoxy-2-hydroxypropyl]-4-[(substituted phenyl)aminocarbonylmethyl]piperazine.

Exemplary compounds are described in Example 1 [Subpart (d)] above and hereinbelow:

1-[3-(phenoxy)-2-hydroxypropyl]-4-(phenylaminocarbonylmethyl)piperazine;

1-[3-(2-methoxyphenoxy)-2-hydroxypropyl]-4-(4-chlorophenyl)aminocarbonylmethyl]piperazine;

1-[3-(2-methoxyphenoxy)-2-hydroxypropyl]-4-[(4-methylphenyl)aminocarbonylmethyl]piperazine;

1-[3-(2-methoxyphenoxy)-2-hydroxypropyl]-4-[(4-methoxyphenyl)aminocarbonylmethyl]piperazine;

1-[3-(2-methoxyphenoxy)-2-hydroxypropyl]-4-[(4-bromophenyl)aminocarbonylmethyl]piperazine;

1-[3-(4-methylthiophenoxy)-2-hydroxypropyl]-4-(phenylaminocarbonylmethyl)piperazine;

1-[3-(2-n-butylthiophenoxy)-2-hydroxypropyl]-4-[(4-chlorophenyl)aminocarbonylmethyl]piperazine;

1-[3-(2-methoxyphenylthio)-2-hydroxypropyl]-4-[(4-methylphenyl)aminocarbonylmethyl]piperazine;

1-[3-(2-methylthiophenylthio)-2-hydroxypropyl]-4-[(4-methoxyphenyl)aminocarbonylmethyl]piperazine;

1-[3-(2-n-butylthiophenylthio)-2-hydroxypropyl]-4-[(3-chlorophenyl)aminocarbonylmethyl]piperazine;

1-[3-(2-methoxyphenoxy)-2-hydroxypropyl]-4-[(2,6-dichlorophenyl)aminocarbnylmethyl]piperazine;

1-[3-(2-methoxyphenoxy)-2-hydroxypropyl]-4-[(2,4,6-trimethylphenyl)aminocarbonylmethyl]piperazine;

1-[3-(2-methoxyphenoxy)-2-hydroxypropyl]-4-[(3,4,5-dimethoxyphenyl)aminocarbonylmethyl]piperazine;

1-[3-(2-methoxyphenoxy)-2-hydroxypropyl]-4-[(4-methylthiophenyl)aminocarbonylmethyl]piperazine;

1-[3-(2-methoxyphenoxy)-2-hydroxypropyl]-4-[(4-ethylthiophenyl)aminocarbonylmethyl]piperazine;

1-[3-(2-methoxyphenoxy)-2-hydroxypropyl]-4-[(4-methylsulfinylphenyl)aminocarbonylmethyl]piperazine;

1-[3-(2-methoxyphenoxy)-2-hydroxypropyl]-4-[(4-n-propylsulfinylphenyl)aminocarbonylmethyl]piperazine;

1-[3-(2-methoxyphenoxy)-2-hydroxypropyl]-4-[(4-trifluoromethylphenyl)aminocarbonylmethyl]piperazine;

1-[3-(2-methoxyphenoxy)-2-hydroxypropyl]-4-[(2-chloro-5-methylphenyl)aminocarbonylmethyl]piperazine;

1-[3-(2-methoxyphenoxy)-2-hydroxypropyl]-4-[(3,5-difluorophenyl)aminocarbonylmethyl]piperazine;

1-[3-(2-methoxyphenoxy)-2-hydroxypropyl]-4-[(2,6-diethoxyphenyl)aminocarbonylmethyl]piperazine;

1-[3-(2-methoxyphenoxy)-2-hydroxypropyl]-4-[(3-bromo-4-ethylphenyl)aminocarbonylmethyl]piperazine;

1-[3-(2-methoxyphenoxy)-2-hydroxypropyl]-4-[(4-n-butylphenyl)aminocarbonylmethyl]piperazine; and 1-[3-(2-methoxyphenoxy)-2-hydroxypropyl]-4-[(4-isobutylphenyl)aminocarbonylmethyl]piperazine.

(e) Similarly, proceeding as in Subpart (a) above but substituting a stoichiometrically equivalent of R- or any one of the substituted R-[1-(phenoxy)-2,3-epoxypropane, and also substituting a stoichiometrically equivalent amount of any one of the substituted phenyl piperazine compounds described in Preparation C above for 1-[(2,6-dimethylphenyl)aminocarbonylmethyl]piperazine, there is obtained the corresponding R-[3-(substituted-phenoxy)-2-hydroxypropyl]-4-[(substituted phenyl)aminocarbonylmethyl]piperazine.

Exemplary compounds of the R- form are named in Example 1, Subparts (b), (c) and (d) above.

(f) Similarly, proceeding as in Subpart (a) above but substituting a stoichiometrically equivalent amount of S- or any one of the S-[1-(optionally substituted phenoxy)]-2,3-epoxypropane compounds described in Preparation D above for 1-(2-methoxyphenyl)-2,3-epoxypropane, and also substituting a stoichiometrically equivalent amount of any one of the substituted phenylaminocarbonyl chloride compounds described in Preparation B [Subpart (b)] above for 1-[(2,6-dimethylphenyl)aminocarbonylmethyl]chloride, there is obtained the corresponding S-[2-(substitutedphenoxy)-2-hydroxypropyl]-4-[(substituted phenyl)aminocarbonylmethyl]piperazine.

(g) Exemplary compounds of the S- form are described in Example 1, Subparts (b), (c) and (d) above.

EXAMPLE 3

(Preparation of Compounds of formula I)

(a) A solution of 0.70 g. of 1-[(2,6-dimethylphenyl)aminocarbonylmethyl]piperazine and 0.71 g of the R-1-phenoxy-2,3-epoxypropane in 20 ml of toluene and 20 ml of methanol is refluxed for 12 hours. Evaporation and chromatography of the residue on silica gel with 10% methanol-methylene chloride gives 0.5 g. of R-1-[3-phenoxy-2-hydroxypropyl]-4-[(2,6-dimethylphenyl)aminocarbonylmethyl]piperazine which is then dissolved in methanol containing excess HCl and precipitated with ether to give the di HCl salt.

(b) Similarly, proceeding as in Subpart (a) above, but substituting the appropriate 1-(substituted arylaminocarbonyl)piperazine from Preparation C for 4-[(2,6-dimethylphenyl)aminocarbonylmethyl]piperazine, the following exemplary compounds are prepared as the dihydrochloride salts:

R-1-[3-phenoxy-2-hydroxypropyl]-4-(phenylaminocarbonylmethyl)piperazine;
R-1-[3-phenoxy-2-hydroxypropyl]-4-[(4-chlorophenyl)aminocarbonylmethyl]piperazine;
R-1-[3-phenoxy-2-hydroxypropyl-4-[(4-methylphenyl)aminocarbonylmethyl]piperazine;
R-1-[3-phenoxy-2-hydroxypropyl]-4-[(4-methoxyphenyl)aminocarbonylmethyl]piperazine;
R-1-[3-phenoxy-2-hydroxypropyl]-4-[(4-chlorophenyl)aminocarbonylmethyl]piperazine; or
R-1-[3-phenoxy-2-hydroxypropyl]-4-[(3-chlorophenyl)aminocarbonylmethyl]piperazine.

EXAMPLE 4

Preparation of Salts of Compounds of formula I (a) A solution of 0.70 g. of 1-[2,6-dimethylphenyl)aminocarbonylmethyl]piperazine and 0.71 g of the 1-phenoxy-2,3-epoxypropane in 20 ml of toluene and 20 ml of methanol is combined and heated at reflux temperature for 12 hours. Evaporation and chromatography of the residue on silica gel with 10% methanol-methylene chloride gives 0.5 g of 1-[3-phenoxy-2-hydroxypropyl]-4-[(2,6-dimethylphenyl)aminocarbonylmethyl]piperazine which is then dissolved in methanol containing excess HCl and precipitated with ether to give the di HCl salt, mp 143°–5° C.

(b) Similarly, proceeding as in Subpart (a) above, but substituting the appropriate 1-(substituted arylaminocarbonyl)piperazine from Preparation C for 1-[(2,6-dimethylphenyl)aminocarbonylmethyl]piperazine, the exemplary compounds are prepared as the dihydrochloride salts.

EXAMPLE 5

(a) Similarly, the compounds of formula I are produced using any of the procedures of Examples 1, 2, 3 or 4 above and the following compounds may be prepared as the hydrochloride or dihydrochloride salts using the procedure of Examples 4 or 6. If desired, the following exemplary compounds and salts may be converted into the free base form by the procedure in Examples 7 and 10 or to another salt by following the procedure of Example 8.

1-[3-(2-methoxyphenoxy)-2-hydroxypropyl]-4-(phenylaminocarbonylmethyl)piperazine and dihydrochloride;

1-[3-(2-methoxyphenoxy)-2-hydroxypropyl]-4-[(4-chlorophenyl)aminocarbonylmethyl]piperazine and dihydrochloride;

1-[3-(2-cyanophenoxy)-2-hydroxypropyl]-4-[(2,6-dimethylphenyl)aminocarbonylmethyl]piperazine and dihydrochloride, di-HCl, mp 213°–215° C.;

1-[3-(2-methoxyphenoxy)-2-hydroxypropyl]-4-[(4-methoxyphenyl)aminocarbonylmethyl]piperazine and dihydrochloride;

1-[3-(2-methoxyphenoxy)-2-hydroxypropyl]-4-[(3,4-dichlorophenyl)aminocarbonylmethyl]piperazine and dihydrochloride;

1-[3-(2-methoxyphenoxy)-2-hydroxypropyl]-4-[(2,6-dimethylphenyl)aminocarbonylmethyl]piperazine and dihydrochloride salt, R- di-HCl, mp 220°–222° C.;

1-[3-(2-methoxyphenoxy)-2-hydroxypropyl]-4-[(3,5-dimethoxyphenyl)aminocarbonylmethyl]piperazine and dihydrochloride;

1-[3-(4-chlorophenoxy)-2-hydroxypropyl]-4-[(2,6-dimethylphenyl)aminocarbonylmethyl)piperazine and dihydrochloride, R,S- di-HCl, mp 205° C.;

1-[3-(phenoxy)-2-hydroxypropyl]-4-[(2,6-dimethylphenyl)aminocarbonylmethyl]piperazine and dihydrochloride, R,S- di-HCl, mp 195° C.;

1-[3-(phenoxy)-2-hydroxypropyl]-4-[(2,5-dimethylphenyl)aminocarbonylmethyl]piperazine and dihydrochloride, R,S- di-HCl, mp 167° C.;

1-[3-(3,4,5-trimethoxyphenoxy)-2-hydroxypropyl]-4-[(2,6-dimethylphenyl)aminocarbonylmethyl]piperazine and dihydrochloride, R,S- di-HCl, mp 210° C.;

1-[3-(2-methoxyphenoxy)-2-hydroxypropyl]-4-[(3,4-dichlorophenyl)aminocarbonylmethyl]piperazine and dihydrochloride, R,S- di-HCl, mp 192° C.;

1-[3-(2-acetylphenoxy)-2-hydroxypropyl]-4-[(2,6-dimethylphenyl)aminocarbonylmethyl]piperazine and dihydrochloride salt, R,S- di-HCl, mp 195° C.;

1-[3-(4-aminocarbonylmethylphenoxy)-2-hydroxypropyl]-4-[(2,6-dimethylphenyl)aminocarbonylmethyl]piperazine and dihydrochloride salt, R,S- di-HCl, mp 148°–150° C.;

1-[3-(2-methoxyphenoxy)-2-hydroxypropyl]-4-[(2,5-dimethylphenyl)aminocarbonylmethyl]piperazine and dihydrochloride, R,S- di-HCl, mp 174° C.;

1-[3-(2-methoxyphenoxy)-2-hydroxypropyl]-4-[(4-methoxyphenyl)aminocarbonylmethyl]piperazine and dihydrochloride, R,S- di-HCl, mp 162° C.;

1-[3-(2-methoxyphenoxy)-2-hydroxypropyl]-4-[(4-fluorophenyl)aminocarbonylmethyl]piperazine and dihydrochloride, R,S- di-HCl, mp 169° C.;

1-[3-(2-methoxyphenoxy)-2-hydroxypropyl]-4-[(4-bromophenyl)aminocarbonylmethyl]piperazine and dihydrochloride, R,S- di-HCl, mp 170° C.;

1-[3-(2-methoxyphenoxy)-2-hydroxypropyl]-4-[(2,6-dimethoxyphenyl)aminocarbonylmethyl]piperazine and dihydrochloride, R,S- di-HCl, mp 155° C.;

1-[3-(2-methoxyphenoxy)-2-hydroxypropyl]-4-[(3,4-dimethoxyphenyl)aminocarbonylmethyl]piperazine and dihydrochloride, R,S-di-HCl, mp 132° C.;

1-[3-(2-methoxyphenoxy)-2-hydroxypropyl]-4-[(4-n-butylphenyl)aminocarbonylmethyl]piperazine and dihydrochloride salt, R,S- di-HCl, mp 180° C.;

1-[3-(2-methoxyphenoxy)-2-hydroxypropyl]-4-[(2-methoxyphenyl)aminocarbonylmethyl]piperazine and dihydrochloride, R,S- di-HCl, mp 196° C.;

1-[3-(2-methoxyphenoxy)-2-hydroxypropyl]-4-[(2,4-dimethylphenyl)aminocarbonylmethyl]piperazine and dihydrochloride, R,S- di-HCl, mp 202° C.;

1-[3-(2-isopropoxyphenoxy)-2-hydroxypropyl]-4-[(2,6-dimethylphenyl)aminocarbonylmethyl]piperazine and dihydrochloride, R,S- di-HCl, mp 180° C.;

1-[3-(2-n-butoxyphenoxy)-2-hydroxypropyl]-4-[(2,6-dimethoxyphenyl)aminocarbonylmethyl]piperazine and dihydrochloride, R,S- di-HCl, mp 160° C.;

1-[3-(1-naphthoxy)-2-hydroxypropyl]-4-[2,6-dimethylphenyl)aminocarbonylmethyl]piperazine and dihydrochloride, R,S- di-HCl, mp 154°-156° C.;

1-[3-(2-methoxyphenoxy)-2-hydroxypropyl]-4-[(3-trifluoromethylphenyl)aminocarbonylmethyl]piperazine and dihydrochloride, R,S-di-HCl, mp 158° C.;

1-[3-(2-methoxyphenoxy)-2-hydroxypropyl]-4-[(2-chloro-5-methylphenyl)aminocarbonylmethyl]piperazine and dihydrochloride;

1-[3-(2-methoxyphenoxy)-2-hydroxypropyl]-4-[(4-methylthiophenyl)aminocarbonylmethyl]piperazine and dihydrochloride;

1-[3-(2-methoxyphenoxy)-2-hydroxypropyl]-4-[(4-n-propylsulfinylphenyl)aminocarbonylmethyl]-piperazine and dihydrochloride;

1-[3-[2-chlorophenoxy)-2-hydroxypropyl]-4-[(3,5-difluorophenyl)aminocarbonylmethyl]piperazine and dihydrochloride;

1-[3-(2-ethylphenoxy)-2-hydroxypropyl]-4-[phenylaminocarbonylmethyl]piperazine and dihydrochloride;

1-[3-(2-methoxyphenoxy)-2-hydroxypropyl]-4-[(2,6-diethoxyphenyl)aminocarbonylmethyl]piperazine and dihydrochloride;

1-[3-(2-methoxyphenoxy)-2-hydroxypropyl]-4-[(3-bromo-4-ethylphenyl)aminocarbonylmethyl]piperazine and dihydrochloride;

1-[3-(4-methoxyphenoxy)-2-hydroxypropyl]-4-(phenylaminocarbonylmethyl)piperazine and dihydrochloride;

1-[3-(2-methoxyphenoxy)-2-hydroxypropyl]-4-[(2-cyanophenyl)aminocarbonylmethyl]piperazine and dihydrochloride;

1-[3-(2-methoxyphenoxy)-2-hydroxypropyl]-4-[(4-acetamidophenyl)aminocarbonylmethyl]piperazine and dihydrochloride;

1-[3-(2-methoxyphenoxy)-2-hydroxypropyl]-4-[(4-N-methylacetamidophenyl)aminocarbonylmethyl]piperazine and dihydrochloride;

1-[3-(2-methoxyphenoxy)-2-hydroxypropyl]-4-[(4-N-n-butylamidophenyl)aminocarbonyl]piperazine and dihydrochloride;

1-[3-(2-acetylphenoxy)-1-[3-(4-n-butanoylphenoxy)-2-hydroxypropyl]-4-[(2,6-dimethylphenyl)aminocarbonylmethyl]piperazine and dihydrochloride;

1-[3-(2-acetylphenoxy)-1-[3-(4-N,N-dimethylaminophenoxy)-2-hydroxypropyl]-4-[(2,6-dimethylphenyl)aminocarbonylmethyl]piperazine and dihydrochloride;

1-[3-(2-acetylphenoxy)-1-[3-(4-N,N-di-n-butylaminophenyl)-2-hydroxypropyl]-4-[(2,6-dimethylphenyl)aminocarbonylmethyl]piperazine and dihydrochloride;

1-[3-(5-n-butylphenoxy)-2-hydroxypropyl]-4-[phenylaminocarbonylmethyl]piperazine and dihydrochloride;

1-[3-(2-methoxyphenoxy)-2-hydroxypropyl]-4-[N-methyl-N-(2,6-diethoxyphenyl)aminocarbonylmethyl]piperazine and dihydrochloride;

1-[3-(phenoxy)-2-hydroxypropyl]-4-[N-methyl-N-(phenyl)aminocarbonyl-1-n-propyl]piperazine and dihydrochloride, di-HCl, mp 210° C.;

1-[3-(4-chlorophenoxy)-2-hydroxypropyl]-4-[N-methyl-N-(phenyl)aminocarbonyl-1-n-propyl]piperazine and dihydrochloride, di-HCl, mp 190° C.;

1-[3-(phenoxy)-2-hydroxypropyl]-4-[N-methyl-N-(phenyl)aminocarbonyl-1-ethyl]piperazine and dihydrochloride, di-HCl, mp 168° C.;

1-[3-(phenoxy)-2-hydroxypropyl]-4-[(phenyl)aminocarbonyl-1-ethyl]piperazine and dihydrochloride, di-HCl, mp 148° C.;

1-[3-(4-chlorophenoxy)-2-hydroxypropyl]-4-[N-methyl-N-(phenyl)aminocarbonyl-1-ethyl]piperazine and dihydrochloride, di-HCl, mp 210° C.;

1-[3-(4-chlorophenoxy)-2-hydroxypropyl]-4-[N-methyl-N-(phenyl)aminocarbonyl-1-n-pentyl]piperazine and dihydrochloride, di-HCl, mp 200° C.;

1-[3-(2-methoxyphenoxy)-2-hydroxypropyl]-4-[4-methylthiophenyl)aminocarbonylmethyl]piperazine and dihydrochloride;

1-[3-(phenylthio)-2-hydroxypropyl]-4-(phenylaminocarbonylmethyl)piperazine and dihydrochloride;

1-[3-(4-methylphenylthio)-2-hydroxypropyl]-4-(phenylaminocarbonylmethyl)piperazine and dihydrochloride.

1-[3-(phenylthio)-2-hydroxypropyl]-4-(phenylaminocarbonyl-1-ethyl)piperazine and dihydrochloride, R,S-di-HCl, mp 146° C.; or 1-[3-(phenylthio)-2-hydroxypropyl]-4-[N-(methyl)-N-(phenyl)aminocarbonylmethyl]piperazine and dihydrochloride, R,S- di-HCl, mp 152° C.

(b) Similarly, proceeding as in Subpart (a) above, but substituting an equivalent amount of R- or S-1-(phenoxy)2,3-epoxypropane for 1-(2-methoxyphenoxy)-2,3-epoxypropane, there is obtained the corresponding salt derivatives having the R- or S-configuration, respectively.

(c) Similarly, proceeding as in Subpart (a) above, but substituting a stoichiometrically equivalent amount of R- or S-1-(optionally substituted phenylthio)-2,3-epoxypropane for R-1-(2-methoxyphenoxy)-2,3-epoxypropane, there is obtained the corresponding salt derivatives having the corresponding R- or S- orientation, respectively.

EXAMPLE 6

Conversion of Free Base to Salt 8.0 g of 1-[3-(2-methoxyphenoxy)-2-hydroxypropyl]-4-[(2,6-dimethylphenyl)aminocarbonylmethyl]piperazine is dissolved in methanol and acidified with methanolic hydrochloric acid. The precipitate is washed with ether to give 7.0 g of the dihydrochloride salt of 1-[3-(2-methoxyphenoxy)-2-hydroxypropyl]-4-[(2,6-dimethylphenyl)aminocarbonylmethyl]piperazine, mp 175°–6° C.

In similar manner, all compounds of formula I in base form prepared in accordance with Examples 1, 2, 3 or 4 can be converted to the corresponding pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 7

Conversion of Salt to Free Base 1.0 g of 1-[3-(2-methoxyphenoxy)-2-hydroxypropyl]-4-[(2,6-dimethylphenyl)aminocarbonylmethyl]piperazine 2HCl suspended in 50 ml of ether is stirred with excess dilute aqueous potassium carbonate solution until the salt is completely dissolved. The organic layer is then separated, washed twice with water, dried over magnesium sulfate and evaporated to yield 1-[3-(2-methoxyphenoxy)-2-hydroxypropyl]-4-[(2,6-dimethylphenyl)aminocarbonylmethyl]piperazine as the free base.

In a similar manner, the acid addition salts prepared in accordance with Example 6 are converted to the corresponding free base.

EXAMPLE 8

Direct Interchange of Acid Addition Salts

1-[3-(2-methoxyphenoxy)-2-hydroxypropyl]-4-[(2,6-dimethylphenyl)aminocarbonylmethyl]piperazine acetate (1.0 g) is dissolved in 50 ml 50% aqueous sulfuric acid, and the solution evaporated to dryness. The product is suspended in ethanol and filtered, air dried and recrystallized from methanol/acetone to yield 1-[3-(2-methoxyphenoxy)-2-hydroxypropyl]-4-[(2,6-dimethylphenyl)aminocarbonylmethyl]piperazine.2HSO$_4$.

EXAMPLE 9

(Preparation of Esters and Dihydrochloride Salts of Formula I)

(a) One g of 1-[3-(2-methoxyphenoxy)-2-hydroxypropyl]-4-[(2,6-dimethylphenyl)aminocarbonylmethyl]piperazine is dissolved in 25 ml of pyridine and cooled in an ice bath to 0°–5° C. Acetic anhydride (0.6 g) is slowly added and the reaction is stirred for 2 hours. After the addition of 100 ml of water, the reaction mixture is extracted twice with 100 ml portions of diethylether. After combining, the ether extract is washed twice with 100 ml of water and evaporated to dryness to produce 1-[3-(2-methoxyphenoxy)-2-acetoxypropyl]-4-[(2,6-dimethylphenyl)aminocarbonylmethyl]piperazine as an oil.

(b) Repeating the above procedure [Subpart (a) of this Example in a similar manner and substituting a stoichiometrically equivalent amount of propionic anhydride; n-butanoic anhydride; n-hexanoic anhydride; n-octanoic anhydride; or n-dodecanoic anhydride for acetic anhydride, there are obtained the following piperazines.

1-[3-(2-methoxyphenoxy)-2-propanoyloxypropyl]-4-[(2,6-dimethylphenyl)aminocarbonylmethyl]piperazine;

1-[3-(2-methoxyphenoxy)-2-n-butanoyloxypropyl]-4-[(2,6-dimethylphenyl)aminocarbonylmethyl]piperazine;

1-[3-(2-methoxyphenoxy)-2-n-hexanoyloxypropyl]-4-[(2,6-dimethylphenyl)aminocarbonylmethyl]piperazine;

1-[3-(2-methoxyphenoxy)-2-n-octanoyloxypropyl]-4-[(2,6-dimethylphenyl)aminocarbonylmethyl]piperazine; or 1-[3-(2-methoxyphenoxy)-2-n-dodecanoyloxypropyl]-4-[(2,6-dimethylphenyl)aminocarbonylmethyl]piperazine.

(c) Repeating the above procedure [Subpart (a) of this example in a similar manner and substituting a stoichiometrically equivalent amount of alkyl anhydride for acetic anhydride and 1-[3-(optionally substituted phenyloxy)-2-hydroxypropyl]-4-[(optionally substituted phenyl)aminocarbonylmethyl]piperazine for 1-[3-(2-methoxyphenoxy)-2-hydroxypropyl]-4-[(2,6-dimethylphenyl)aminocarbonylmethyl]piperazine, there is obtained the corresponding 1-[3-(optionally substituted-phenoxy)-2-alkanoyloxy-propyl)]-4-[(optionally substituted phenyl)aminocarbonyl-methyl]piperazine.

(d) The compounds described in Subparts (a), (b) or (c) of this Example when treated with excess hydrochloric as described in Example 8 produce the corresponding 1-[3-(optionally substituted phenoxy)-2-alkanoyloxypropyl]-4-[(optionally substituted phenyl)aminocarbonylmethyl]piperazine dihydrochloride.

In all of the reactions described by Subparts (a), (b), (c) and (d) of this Example, optionally substituted thiophenoxy compounds may be substituted for the phenoxy compounds, and the stereochemistry of the compound of formula I is not changed.

EXAMPLE 10

A solution of 3.5 g of 1-[3-(2-methoxyphenoxy)-2-hydroxypropyl]-4-[(2,6-dimethylphenyl)aminocarbonylmethyl]piperazine dihydrochloride salt in water (50 ml) is adjusted to pH 12 with ammonium hydroxide solution and extracted with methylene chloride. The methylene chloride is evaporated to afford 3 g of 1-[3-(2-methoxyphenoxy)-2-hydroxypropyl]-4-[(2,6-dimethylphenyl)aminocarbonylmethyl]piperazine as the free base.

In a similar manner, the acid addition salts prepared in accordance with Examples 6 and 8 are converted to the corresponding free base.

EXAMPLE 11

The following example illustrates the preparation of representative pharmaceutical formulations containing an active compound of formula I, e.g., 1-[3-(2-methoxyphenoxy)-2-hydroxypropyl]-4-[(2,6-dimethylphenyl)aminocarbonylmethyl]piperazine.

| I.V. Formulation | |
| --- | --- |
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

In Examples 11 through 17, the active ingredient is 1-[1-(phenoxy)-2-hydroxypropyl]-4-[(2,6-dimethylphenyl)aminocarbonylmethyl]piperazine dihydrochloride. Other compounds of formula I and the pharmaceutically acceptable salts thereof may be substituted therein.

EXAMPLE 12

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 13

| Ingredients | Quantity per capsule, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 14

| Ingredients | Quantity per tablet, mgs. |
| --- | --- |
| Active ingredient | 1 |
| cornstarch | 50 |
| lactose | 145 |
| magnesium stearate | 5 |

The above ingredients are mixed intimately and pressed into single scored tablets.

EXAMPLE 15

| Ingredients | Quantity per capsule, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 16

| Ingredients | Quantity per capsule, mgs. |
| --- | --- |
| Active ingredient | 150 |
| lactose | 92 |

The above ingredients are mixed and introduced into a hard-shell gelatin capsule.

EXAMPLE 17

An injectable preparation buffered to a pH of 7 is prepared having the following composition:

| Ingredients | |
| --- | --- |
| Active ingredient | 0.2 g |
| KH$_2$PO$_4$ buffer (0.4 M solution) | 2 ml |
| KOH (1 N) q.s. | to pH 7 |
| water (distilled, sterile) q.s. | to 20 ml |

EXAMPLE 18

An oral suspension is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water q.s. to | 100 ml |

In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings. While the present invention has been described with reference to the specific embodiments thereof, it should be understood by those skilled in this art that various changes may be made and equivalents may be substituted without departing from the true spirit and scope of the invention.

What is claimed is:

1. A compund of the formula:

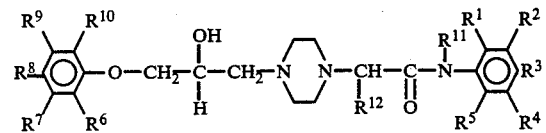

and the pharameutically acceptable esters and acid addition salts thereof, wherein:

R1 and R5 are each methyl

R2 and R3 and R4 are each hydrogen and R6 to R12 are each hydrogen, i.e., 1-[3-phenoxy-2-hydroxypropyl]-4-[2,6-dimethylphenyl)-aminocarbonylmethyl]-piperazine, and the pharaceutically acceptable esters and acid addition salts thereof.

2. A compound of the formula:

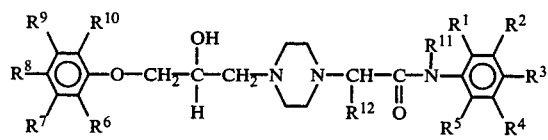

and the pharmaceutically acceptable esters and acid addition salts thereof, wherein:

$R^1$ and $R^5$ are each methyl $R^2$, $R^3$, and $R^4$ are each hydrogen, $R^6$ is methoxy and $R^7$ to $R^{12}$ are each hydrogen, i.e., 1-[3-(2-methoxyphenoxy)-2-hydroxypropyl]-4-[(2,6,-dimethylphenyl)-aminocarbonylmethyl]-piperazine, and the pharaceutically acceptable esters and acid addition salts thereof.

3. A compound of the formula:

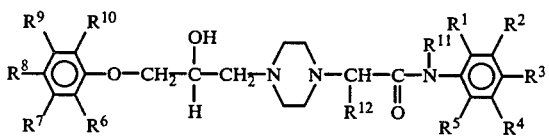

and the pharmaceutically acceptable esters and acid addition salts thereof, wherein:

$R^1$ and $R^5$ are each methyl;

$R^2$, $R^3$, and $R^4$ are each hydrogen, $R^6$ is cyano and $R^7$ to $R^{12}$ are each hydrogen, i.e., 1-[3-(2-cyanohenoxy)-2-hydroxypropyl]-4-[2,6-dimethylphenyl)aminocarbonylmethyl]piperazine.

* * * * *